(12) United States Patent
Shahoian

(10) Patent No.: US 8,702,722 B2
(45) Date of Patent: Apr. 22, 2014

(54) SYSTEM AND METHOD FOR THE SIMULTANEOUS AUTOMATED BILATERAL DELIVERY OF PRESSURE EQUALIZATION TUBES

(75) Inventor: Erik James Shahoian, San Ramon, CA (US)

(73) Assignee: Acclarent, Inc., Menlo Park, CA (US)

( * ) Notice: Subject to any disclaimer, the term of this patent is extended or adjusted under 35 U.S.C. 154(b) by 0 days.

(21) Appl. No.: 13/164,993

(22) Filed: Jun. 21, 2011

(65) Prior Publication Data

US 2011/0288559 A1 Nov. 24, 2011

Related U.S. Application Data

(63) Continuation of application No. 11/749,734, filed on May 16, 2007, now Pat. No. 8,052,693.

(60) Provisional application No. 60/912,902, filed on Apr. 19, 2007.

(51) Int. Cl.
*A61F 11/00* (2006.01)

(52) U.S. Cl.
USPC .......................................................... 606/109

(58) Field of Classification Search
USPC .............. 604/8, 244; 606/108, 109; 623/1.11, 623/1.12
See application file for complete search history.

(56) References Cited

U.S. PATENT DOCUMENTS

| | | | |
|---|---|---|---|
| 858,673 A | 7/1907 | Roswell | |
| 1,920,006 A | 7/1933 | Dozier | |
| 3,741,197 A | 6/1973 | Sanz et al. | |
| 3,888,258 A * | 6/1975 | Akiyama | 606/109 |
| 3,897,786 A | 8/1975 | Garnett et al. | |
| 3,913,584 A | 10/1975 | Walchle et al. | |
| 3,948,271 A | 4/1976 | Akiyama | |
| 3,991,755 A | 11/1976 | Vernon et al. | |
| 4,468,218 A | 8/1984 | Armstrong | |
| 4,473,073 A | 9/1984 | Darnell | |
| 4,564,009 A | 1/1986 | Brinkhoff | |
| 4,712,537 A * | 12/1987 | Pender | 600/200 |
| 4,968,296 A * | 11/1990 | Ritch et al. | 604/8 |
| 4,971,076 A | 11/1990 | Densert et al. | |
| 5,026,378 A | 6/1991 | Goldsmith, III | |
| 5,044,373 A | 9/1991 | Northeved et al. | |

(Continued)

FOREIGN PATENT DOCUMENTS

CN 86105171 3/1987
DE 19618585 11/1997

(Continued)

OTHER PUBLICATIONS

U.S. Appl. No. 61/085,360, filed Jul. 31, 2008.

(Continued)

*Primary Examiner* — Ryan Severson
*Assistant Examiner* — Jonathan W Miles
(74) *Attorney, Agent, or Firm* — Frost Brown Todd LLC

(57) ABSTRACT

Systems and methods for treating a patient having a head with a first ear and a second ear, function by aligning a first device with a tympanic membrane of the first ear; inputting a command to an input device operatively coupled to the first device to generate a signal; and actuating the first device in response to the signal so as to drive a penetrator of the device through the tympanic membrane.

19 Claims, 32 Drawing Sheets

(56) References Cited

U.S. PATENT DOCUMENTS

| | | | |
|---|---|---|---|
| 5,053,040 | A | 10/1991 | Goldsmith, III |
| 5,107,861 | A | 4/1992 | Narboni |
| 5,254,120 | A | 10/1993 | Cinberg et al. |
| 5,261,903 | A | 11/1993 | Dhaliwal et al. |
| D352,780 | S | 11/1994 | Glaeser et al. |
| 5,421,818 | A | 6/1995 | Arenberg |
| 5,466,239 | A | 11/1995 | Cinberg et al. |
| 5,496,329 | A * | 3/1996 | Reisinger ............... 606/109 |
| D378,611 | S | 3/1997 | Croley |
| 5,610,988 | A | 3/1997 | Miyahara |
| 5,643,280 | A | 7/1997 | Del Rio et al. |
| 5,674,196 | A | 10/1997 | Donaldson et al. |
| D387,863 | S | 12/1997 | Herman et al. |
| 5,707,383 | A | 1/1998 | Bays et al. |
| 5,792,100 | A | 8/1998 | Shantha |
| 5,827,295 | A | 10/1998 | Del Rio et al. |
| 5,893,828 | A | 4/1999 | Uram |
| D418,223 | S | 12/1999 | Phipps et al. |
| D420,741 | S | 2/2000 | Croley |
| 6,045,528 | A | 4/2000 | Arenberg et al. |
| D424,197 | S | 5/2000 | Sydlowski et al. |
| 6,059,803 | A | 5/2000 | Spilman |
| D426,135 | S | 6/2000 | Lee |
| 6,137,889 | A | 10/2000 | Shennib et al. |
| 6,183,469 | B1 | 2/2001 | Thapliyal et al. |
| 6,200,280 | B1 | 3/2001 | Brenneman et al. |
| 6,206,888 | B1 * | 3/2001 | Bicek et al. ............... 606/108 |
| 6,245,077 | B1 | 6/2001 | East et al. |
| 6,251,121 | B1 | 6/2001 | Saadat |
| D450,843 | S | 11/2001 | McGuckin, Jr. et al. |
| 6,358,231 | B1 | 3/2002 | Schindler et al. |
| 6,440,102 | B1 | 8/2002 | Arenberg et al. |
| 6,475,138 | B1 | 11/2002 | Schechter et al. |
| 6,514,261 | B1 * | 2/2003 | Randall et al. ............... 606/108 |
| 6,522,827 | B1 | 2/2003 | Loeb et al. |
| 6,645,173 | B1 | 11/2003 | Liebowitz |
| 6,770,080 | B2 | 8/2004 | Kaplan et al. |
| 6,916,159 | B2 | 7/2005 | Rush et al. |
| 7,127,285 | B2 | 10/2006 | Henley et al. |
| D535,027 | S | 1/2007 | James et al. |
| 7,344,507 | B2 * | 3/2008 | Briggs et al. ............... 600/583 |
| 7,351,246 | B2 | 4/2008 | Epley |
| 7,381,210 | B2 | 6/2008 | Zarbatany et al. |
| D595,410 | S | 6/2009 | Luzon |
| D598,543 | S | 8/2009 | Vogel et al. |
| D622,842 | S | 8/2010 | Benoist |
| 8,052,693 | B2 | 11/2011 | Shahoian |
| 8,249,700 | B2 | 8/2012 | Clifford et al. |
| 2002/0026125 | A1 | 2/2002 | Leysieffer |
| 2002/0069883 | A1 | 6/2002 | Hirchenbain |
| 2002/0111585 | A1 | 8/2002 | Lafontaine |
| 2002/0138091 | A1 | 9/2002 | Pflueger |
| 2002/0169456 | A1 | 11/2002 | Tu et al. |
| 2003/0060799 | A1 | 3/2003 | Arenberg et al. |
| 2004/0054339 | A1 | 3/2004 | Ciok et al. |
| 2005/0182385 | A1 | 8/2005 | Epley |
| 2005/0235422 | A1 | 10/2005 | Wallace |
| 2005/0240147 | A1 | 10/2005 | Makower et al. |
| 2006/0142700 | A1 | 6/2006 | Sobelman et al. |
| 2006/0155304 | A1 | 7/2006 | Kaplan et al. |
| 2007/0233222 | A1 | 10/2007 | Roeder et al. |
| 2008/0051804 | A1 | 2/2008 | Cottler et al. |
| 2008/0262468 | A1 | 10/2008 | Clifford et al. |
| 2008/0262508 | A1 | 10/2008 | Clifford et al. |
| 2009/0209972 | A1 * | 8/2009 | Loushin et al. ............... 606/109 |
| 2009/0299344 | A1 | 12/2009 | Lee et al. |
| 2010/0041447 | A1 | 2/2010 | Graylin |
| 2010/0061581 | A1 | 3/2010 | Soetejo et al. |
| 2012/0310145 | A1 | 12/2012 | Clifford et al. |
| 2013/0090544 | A1 | 4/2013 | Clifford et al. |

FOREIGN PATENT DOCUMENTS

| | | |
|---|---|---|
| EP | 0214527 | 1/1991 |
| FR | 2526656 | 11/1983 |
| WO | WO 2006/119512 | 11/2006 |
| WO | WO 2008/030485 | 3/2008 |
| WO | WO 2008/036368 | 3/2008 |
| WO | WO 2009/010788 | 1/2009 |

OTHER PUBLICATIONS

U.S. Appl. No. 11/749,729, filed May 16, 2007.
U.S. Appl. No. 11/749,733, filed May 16, 2007.
U.S. Appl. No. 11/962,063, filed Dec. 20, 2007.
U.S. Appl. No. 11/962,073, filed Dec. 20, 2007.
Comeau, M. et al. 'Local Anesthesia of the Ear by Iontophresis' (1973) Arch Otolaryngol. vol. 98 pp. 114-120.
Comeau, M. et al. 'Anesthesia of the Human Tympanic Membrane by Iontophoresis of a Local Anesthetic 11978' The Larynogoscope vol. 88 pp. 277-285.
Echols, D.F. et al. 'Anesthesia of the Ear by Iontophoresis of Lidocaine' (1975) Arch Otolaryngol. vol. 101, pp. 418-421.
Epley, J.M. 'Modified Technique of Iontophoretic Anesthesia for Myringotomy in Children' (1977) Arch Otolaryngol. vol. 103 pp. 358-360.
Hasegawa, M. et al. 'Iontophorectic Anaesthesia of the Tympanic Membrane' (1978) Clinical Otolaryngoloy. vol. 3 pp. 63-66.
Medtronic XOMED. Activent®, Antimicrobial Ventilation Tubes. 4 pages.
Micromedics Innovative Surgical Products [retrieved on Jul. 15, 2010] Retrieved from the Internet <URL: http://www.micromedics-usa.com/products/otology/micromedicstubes.htm. 7 pages.
Plenum' Compact Oxford English Dictionary <http://oxford-dictionaries.com/definition/english/plenum>.
Plenum' Merriam-Webster's Online Dictionary, 11th Edition. <http://www.merriam-webster.com/dictionary/plenum>.
Ramsden, R.T. et al. 'Anaesthesia of the Typanic Membrane Using Iontophoresis' (1977) The Journal of Layngology and Otology. vol. 56, No. 9. pp. 779-785.
International Search Report dated Sep. 3, 2008 re: PCT/US2008/60779.
International Search Report dated Nov. 6, 2009 re: PCT/2009/052395.
International Search Report dated Jun. 30, 2010 re: PCT/US2009/069388.
International Search Report dated Aug. 27, 2010 re: PCT/US2010/042128.
International Search Report dated Feb. 17, 2011 re: PCT/US2010/058718.
Australian Office Action, Patent Examination Report No. I, dated Aug. 8, 2012 re AU 2008242735.
Chinese Office Action, First Office Action, dated Jul. 12, 2011 for CN 200880020861.9.
Chinese Office Action, Second Office Action, dated Dec. 30, 2011 for CN 200880020861.9.
Japanese Office Action dated Nov. 20, 2012 for JP 2010-504267.
U.S. Appl. No. 60/912,902, filed Apr. 19, 2007.

* cited by examiner

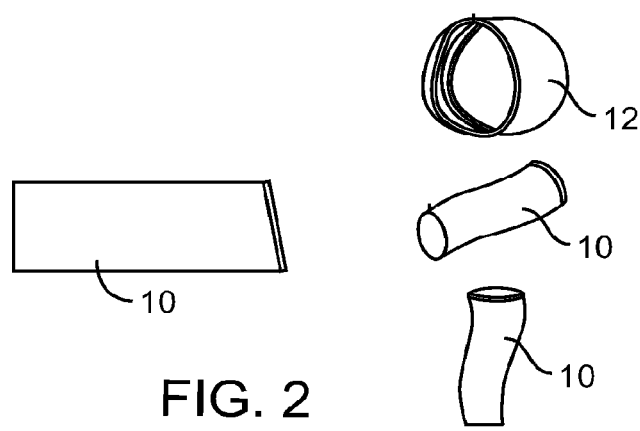
FIG. 2
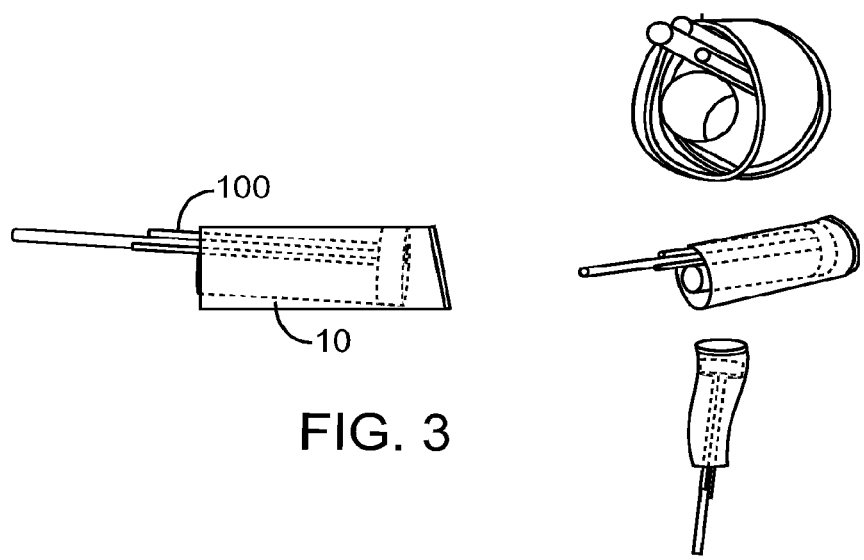
FIG. 3
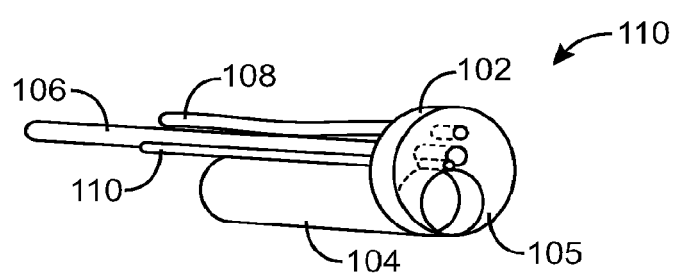
FIG. 4

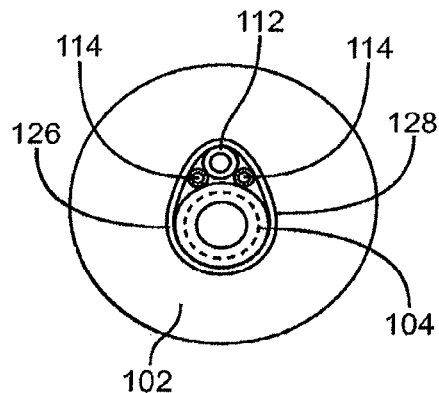
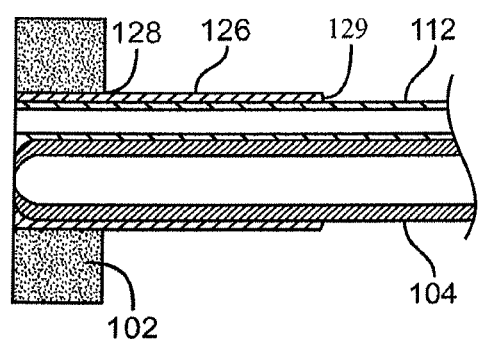
FIG. 14B    FIG. 14A
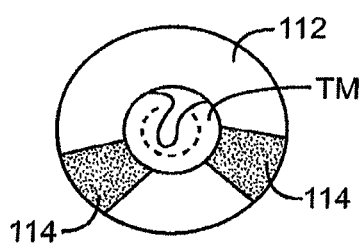
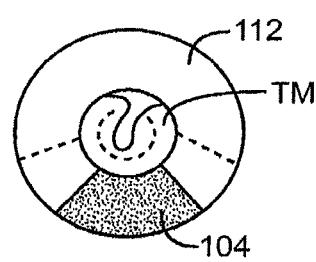
FIG. 15A    FIG. 15B
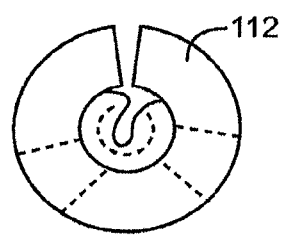
FIG. 15C

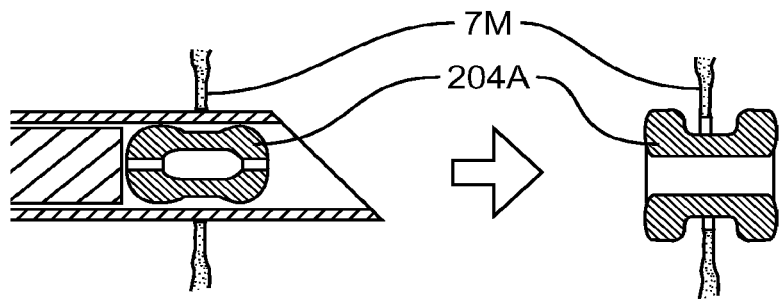
FIG. 42A   FIG. 42B
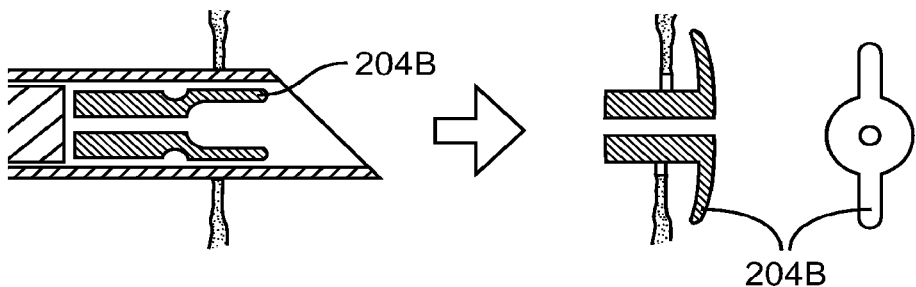
FIG. 43A   FIG. 43B
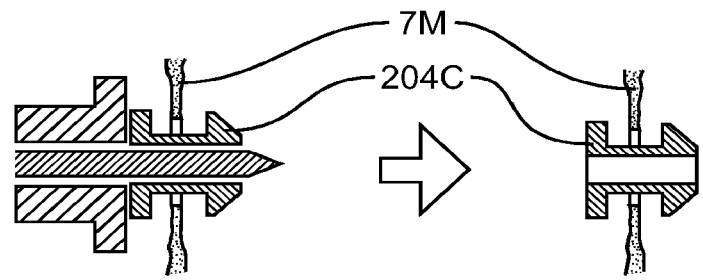
FIG. 44A   FIG. 44B
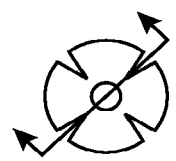 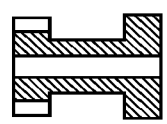
FIG. 44C   FIG. 44D

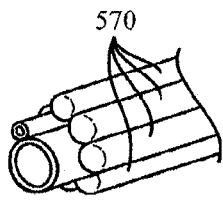
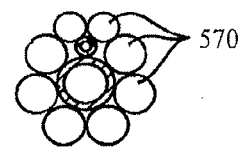
FIG. 46A          FIG. 46B
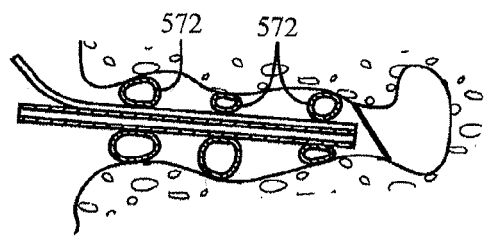
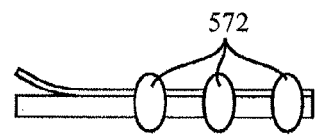
FIG. 47A          FIG. 47B
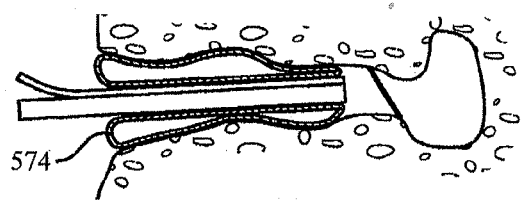
FIG. 48A          FIG. 48B
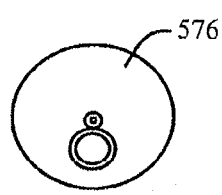
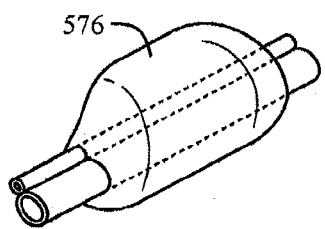
FIG. 49A          FIG. 49B HOW BEAM "SPOT" APPEARS ON TARGET SURFACE AT DIFFERENT RANGES:
I = TOO CLOSE
II = JUST RIGHT
III = TOO FAR

TOO CLOSE    JUST RIGHT    TOO FAR

SYSTEM AND METHOD FOR THE SIMULTANEOUS AUTOMATED BILATERAL DELIVERY OF PRESSURE EQUALIZATION TUBES

CROSS-REFERENCES TO RELATED APPLICATIONS

The present application is a continuation of U.S. application Ser. No. 11/749,734, filed May 16, 2007 now U.S. Pat. No. 8,052,693, which claims priority to U.S. Provisional Patent Application No. 60/912,902, filed Apr. 19, 2007, the teachings of which are incorporated herein by reference.

BACKGROUND OF THE INVENTION

The present invention is generally related to medical devices and apparatus. In particular, the invention provides systems, methods, devices, and kits for treating a patient's ear. In one embodiment, the invention provides a system and method for tympanotomy, tympanostomy, or myringotomy with or without tympanostomy tube placement, and for other procedures requiring manipulation or penetration of the tympanic membrane such as tympanocentesis.

Otitis media is among the most common diagnoses made by pediatricians. A majority of children may have at least one episode of otitis media ("earache") prior to their third birthday. Otitis media is often caused by an inability of the eustachian tube to drain fluid from the middle ear. Otitis media is often treated with antibiotics.

A significant number of children exhibit recurrent episodes of otitis media and/or otitis media with effusion. Treatment of these more severe cases often involves the placement of a tympanostomy tube through the tympanic membrane so as to provide adequate drainage of the middle ear and reduce the likelihood of future infections. Tympanostomy tubes provide fluid communication between the middle and outer ear, and typically fall out spontaneously within about a year of placement. Tympanostomy tube placement is among the most frequent surgical procedures performed in the pediatric population. It has been estimated that more than a million tympanostomy tubes may be placed each year, with typical patients being between about 18 months and 7 years of age at the time of the procedure.

Tympanostomy tube placement is typically performed in an out-patient surgery setting under general anesthesia. The external auditory canal and tympanic membrane are examined under microscopic visualization through a hand-held conical shaped speculum. An incision or myringotomy is made in the tympanic membrane, typically using an elongate, small profile scalpel which the physician extends through the conical speculum. Fluid may be aspirated through the myringotomy, and a tympanostomy tube is placed so as to extend through the tympanic membrane.

A wide variety of tympanostomy tubes are commercially available, and a still wider variety of others tubes have been proposed. A number of systems have been proposed to both perform the myringotomy and deploy the tympanostomy tube with a single treatment assembly. In recent years, more complex and expensive systems have been proposed for diagnosis or treatment of the tissues of the ear, including systems using laser energy for forming a myringotomy, video systems for imaging of the ear canal, and the like. These various alternatives have, not surprisingly, been met with varying degrees of acceptance.

A standard tympanostomy tube placement procedure is both effective and quite safe. Nonetheless, further improvements would be desirable. In particular, there are both risks and costs associated with out-patient surgical procedures performed under general anesthesia. For example, a significant portion of the risk and cost of tympanostomy tube placement is associated with the administration of general anesthesia, i.e., the need for an operating room, the presence of an anesthesiologist, and related recovery room time.

In light of the above, it would be desirable to provide improved devices, systems, methods, and kits for treatment of the tissue structures within the auditory canal. It would generally be beneficial if these improvements facilitated myringotomy with or without tympanostomy tube placement without having to resort to general anesthesia, thereby allowing these common procedures to be performed in a doctor's office (rather than in an outpatient surgical facility). There are some studies that suggest placing children under general anesthesia may induce neurodegeneration in the developing brain. Therefore, it would be desirable to provide devices, systems, methods and kits for treatment of the tissue structures within the auditory canal without using general anesthesia. It would further be desirable if these improvements could be provided while decreasing the overall procedure time, and ideally, at a reduced overall procedure cost.

BRIEF SUMMARY OF THE INVENTION

The present invention provides systems and methods for the provision of painless, simultaneous, bilateral treatment of the target tissues of the ear of children suffering from recurrent otitis or otitis media with effusion in an office-based procedure with awake, mobile patients, created to manage the child's anxiety.

In one aspect, the present invention provide systems and methods for treating a patient having a head with a first ear and a second ear that function by aligning a first device with a tympanic membrane of the first ear; inputting a command to an input device operatively coupled to the first device to generate a signal; and actuating the first device in response to the signal so as to drive a penetrator of the device through the tympanic membrane.

In another aspect, the present invention provides systems and methods for the direct visualization and the targeting and range finding for the target tissue of the ear which facilitate the visual and/or optical monitoring and thus a more effective treatment of the target tissue region. In one aspect, the present invention provides systems and methods that enable a clinician to specify a range or distance or have mechanisms like visualization or markers that can locate or appreciate the distance from the treatment device and the tympanic membrane.

Advantageously, such systems and methods facilitate performing treatment procedures such as myringotomy, tympanostomy tube placement, tympanocentisis and the like, under local (rather than general) anesthesia, often in a doctor's office (rather than an out-patient surgical facility).

For a further understanding of the nature and advantages of the invention, reference should be made to the following description taken in conjunction with the accompanying figures. It is to be expressly understood, however, that each of the figures is provided for the purpose of illustration and description only and is not intended as a definition of the limits of the embodiments of the present invention.

BRIEF DESCRIPTION OF THE DRAWINGS

FIG. 2 illustrates views of a simplified ear canal.

FIG. 3 illustrates the insertion of an exemplary guide block in accordance with the embodiments of the present invention into the ear canal.

FIG. 4 illustrates various details of the guide block of FIG. 3.

FIGS. 14A-B illustrate detailed sectional views for the guide block system of FIG. 12.

FIGS. 15A-C illustrate exemplary views seen by the endoscope of FIG. 12, when the guide block system is in place in the patient's ear.

FIGS. 42A-B illustrate a PE tube that is delivered from the inside of a cutting tool.

FIGS. 43A-B illustrate a grommet or T-tube type PE tube that is delivered from the inside of a cutting tool.

FIGS. 44A-B illustrate a PE tube that is delivered on the outside of a cutting tool.

FIGS. 44C-D illustrate flanges on a PE tube that have cut-outs to allow for the easier passage and its deflection through the TM.

FIGS. 46A-B illustrate the use of multiple longitudinal balloons that are used to stabilize the guide block tubes within the ear canal.

FIGS. 47A-B illustrate the use of multiple circumferential balloons that are used to stabilize the guide block tubes within the ear canal.

FIGS. 48A-B illustrate the use of a compliant balloon that is used to stabilize the guide block tubes within the ear canal.

FIGS. 49A-B illustrate the use of an offset balloon that is used to stabilize the guide block tubes within the ear canal.

DETAILED DESCRIPTION OF THE INVENTION

The embodiments of the present invention provide systems and methods for the provision of painless, simultaneous, bilateral treatment of the target tissues of the ear of children suffering from recurrent otitis or otitis media with effusion in an office-based procedure in awake, mobile patients, designed to manage the child's and the parent's anxiety.

In one aspect, the present invention is directed toward a suite of medical devices that shares a common support structure that is used to align various therapeutic devices with the target tissues of the ear of children. In one embodiment, the suite of medical devices can be used to insert pressure equalization (PE) tubes in the tympanic membranes without reliance on general anesthesia. The novel suite of medical devices enable the performance of an in-office procedure for the placement of PE tubes in a patient's tympanic membranes that does not require general anesthesia that can be completed within a short period of time (e.g., 30 minutes); that can treat both ears at the same time (e.g., simultaneous bilateral); is suitable for young patients (e.g., 18 months to 7 years old), where the management of anxiety and minimal interventions are desirable. Such therapeutic procedures also benefit from the reduction of risks associated with the traditional surgical procedure.

The novel suite of medical devices that share a common support structure include devices for supporting, aligning and guiding the one or more medical devices within the ear canal via a guide block; devices for positioning the guide block;

devices for stabilizing the guide block; devices for applying a local pain inhibitor to both ears before initiation of the therapeutic treatment; devices for visualization; and devices for penetrating the tympanic membranes and for delivering PE tubes. In addition, the common support structure is coupled with a system that is used to preoccupy the patient with either or both of an audio track, where the therapeutic treatment may be synchronized with the audio track; or a video, where the therapeutic treatment may be synchronized with the video. In this manner, the child patient is distracted while any combination of the above devices are being utilized. For example, as the child patient is listening to a sound track for a video, the volume of the sound track is increased at critical times, when the above devices could also create a loud noise that would otherwise be heard by the patient had he/she not been distracted by the sound track. Each of these medical devices is described below in further details.

Figure 1:
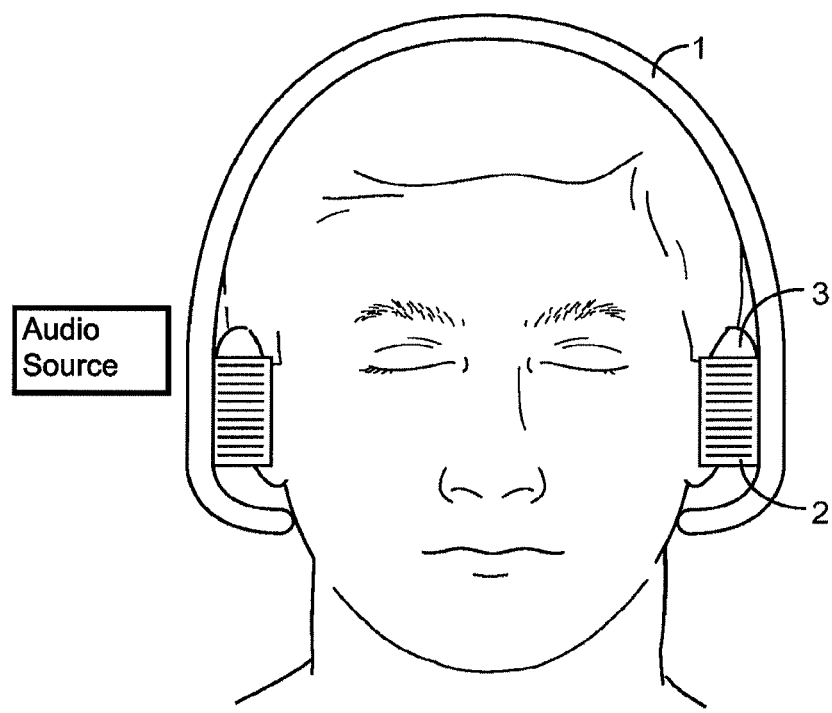
FIG. 1 illustrates the simplified support structure that is worn on the patient's head.

FIG. 1 illustrates the simplified support structure 1 that is worn on the patient's head while the patient is awake and upright. The support structure 1 is configured to hold the one or more novel suite of medical devices 2 described above in alignment with the patient's ears 3. As can be seen in FIG. 1, the support structure 1 can have an alignment structure with a first body engaging the first ear, a second body engaging the second ear, and a member extending around the head of the patient between the first and second body.

FIGS. 2-10 illustrate a sequence of therapeutic procedures that can be undertaken by using the suite of medical devices that share a common support structure that is used to align various therapeutic devices with the target tissues of the ear of children. FIG. 2 illustrates views of a simplified ear canal. As can be seen in FIG. 2, the ear canal 10 is approximately 19 mm long and has an average diameter of approximately 7 mm. It has a non-uniform shape, terminating at the tympanic membrane 12 or the ear drum 12. As set forth above, the suite of medical devices can be used to insert pressure equalization (PE) tubes in the tympanic membranes in a non-surgical procedure that does not require general anesthesia. As a first step, FIG. 3 illustrates the insertion of an exemplary guide block 100 in accordance with the embodiments of the present invention into the ear canal 10. As is shown in FIG. 4 the guide block 100 includes a foam block or disk 102 at its distal end. The foam block 102 is configured to fit within the ear canal 10 near the tympanic membrane 12. The foam block 102 holds in alignment a guide tube 104. The guide tube 104 extends through the foam block and is configured to be located near the tympanic membrane (TM). The guide tube 104 has a soft tip 105 at its distal end. The foam block 102 also holds in alignment a tube 106 that can be used to deliver medication into the space between the foam block 102 and the TM. The tube 106 can also be used as a guide for an image capture device such as an endoscope. The foam block 102 also can hold in alignment a vent tube 108 that is used to vent the space between the foam block 102 and the TM during the treatment of the space. In addition, the foam block 102 also holds in alignment an electrode and a low gauge electrical wire 110 to enable the iontophoresis module. As can be seen in FIG. 4, the inserted guide block 100 fits within the ear canal 10, and the distal end of the guide block is located near the tympanic membrane 12. In one embodiment, the guide block 100 can be aligned to target PE tube placement using an in-situ vision system that can be fed in through the tube 106. Alternatively, the vision system can be configured to support distance registration, such that the distance between the guide block 100 and the TM 12 can be managed.

Figure 5:
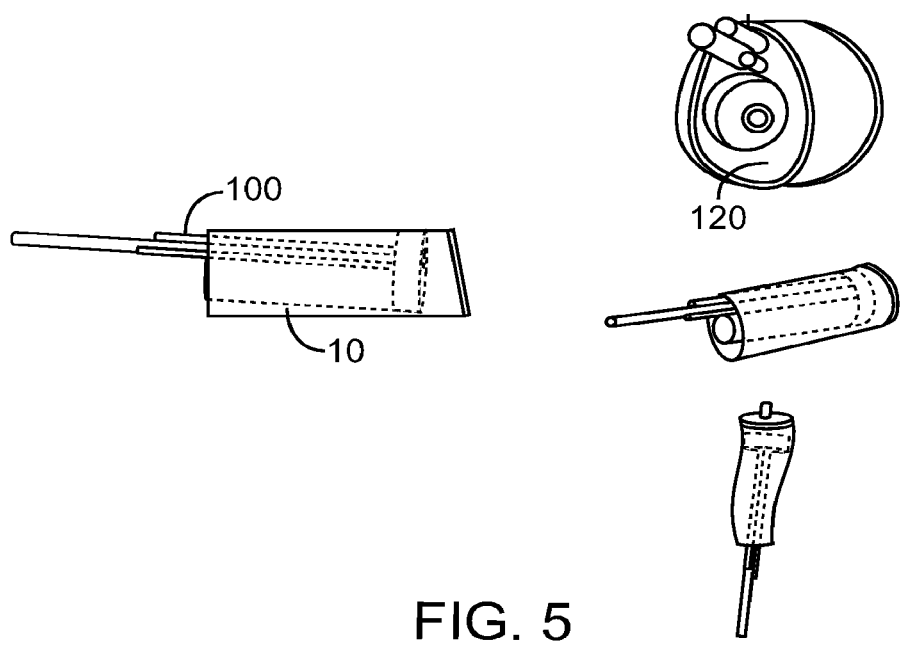
FIG. 5 illustrates the stabilization of the guide block.

FIG. 5 illustrates the stabilization of the guide block 100 within the ear canal 10. The guide block 100 can be stabilized within the ear canal 10 by the insertion of a hardenable material 120 about the guide block. The injectable material 120 has a workable state allowing adjustment to alignment between the guide block support structure and the target tissue of the ear. The injectable material 120 also has a hardened state for stabilizing the guide block support structure relative to the target tissue. The workable state can be time dependent or activated. In one embodiment, the impression material can harden in a matter of minutes. In other configurations, the impression material may be workable until a hardening agent is added, as is described below.

The stabilized guide block 100 can be used to receive modules with each module capable of completing a different function. For example, the first module can be used for range finding/distance setting; then that module can be removed from the guide block and a second module that can be an iontophoresis unit is inserted. Thereafter, the iontophoresis unit is removed and the next (e.g., actuator module) can be inserted. The guide block 100 can be used for a drug delivery/injection module for acute otitis media, and it can also be used for a PE tube delivery module for otitis media with effusion.

Figure 6:
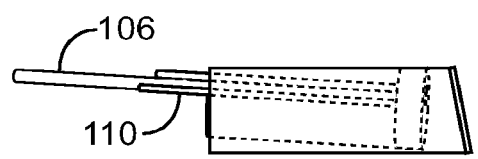
FIG. 6 illustrates pain inhibitor insertion and iontophoresis activation.

FIG. 6 illustrates the application of a local pain inhibitor to the ears for example, before the myringotomy and the PE tube placement. In this manner, the myringotomy and the PE tube placement can occur while the patient is awake. The local pain inhibitor can be lidocaine with or without epinephrine. Once the pain inhibitor has been inserted into the distal space between the guide block 100 and the TM 12 via tube 106 it is iontophoretically activated by coupling the electrode 110 to the iontophoresis module 4. The iontophoresis module can also be used in the ear canal to deliver antibiotic and/or anti-inflammatory agents for transtympanic delivery across inflamed tissue. The guide block 100 and the iontophoresis module can be used for local delivery of not just a pain inhibitor through the ear. The guide block 100 and the iontophoresis module can be used for local delivery of other therapeutics such as mucolytics, antibiotics, steroids, surfactants, and so on, either before or after a myringotomy and/or a tympanocentisis, or prior to the piercing of the TM to help position and stabilize the tissue to aid in the actual incision. The drug delivery may also be useful in the case of a retracted ear drum. The iontophoresis system is able to provide a well-tolerated method for providing anesthesia with lidocaine in a relatively short time to the patient that does not suffer from the symptoms associated with the systemic delivery of this drug.

Figure 7:
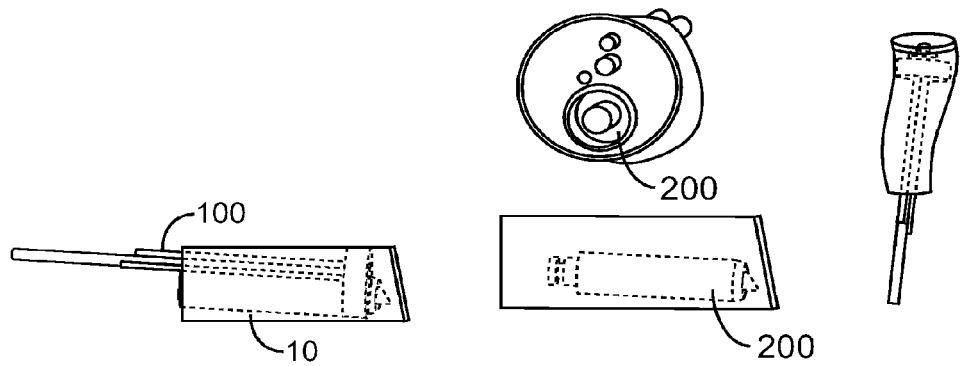
FIG. 7 illustrates the placement of the combined TM penetrator and delivery device.
Figure 8:
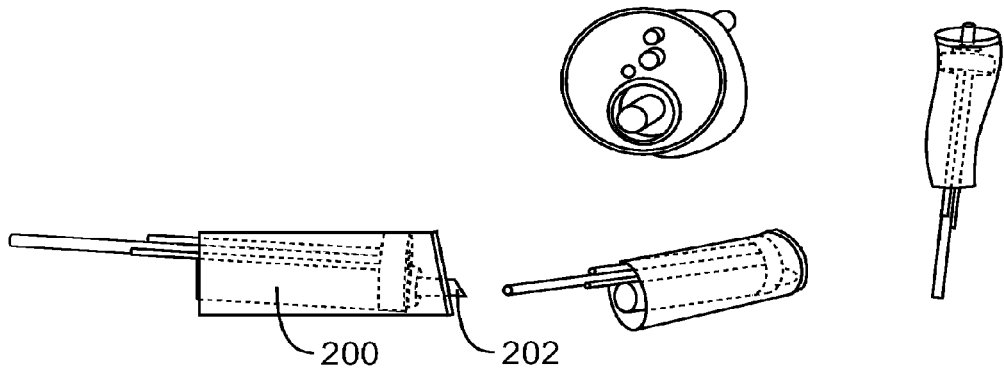
FIG. 8 illustrates the penetration of the TM.
Figure 9:
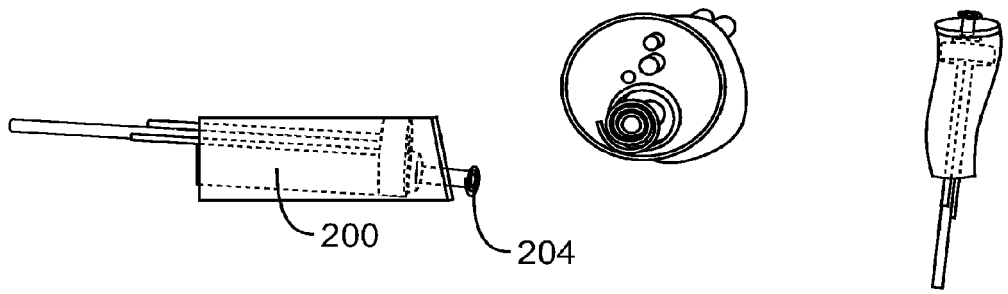
FIG. 9 illustrates the PE tube delivery.

FIG. 7 illustrates the placement of the combined TM penetrator and delivery device 200, in accordance with one embodiment of the present invention. The combined TM penetrator and delivery device 200 can be inserted into the delivery system guide 104. The combined TM penetrator and delivery device 200 once in place can advance a lance 202 at its distal end to penetrate the TM membrane. Once the TM has been penetrated, the lance 202 can be retracted so as to deploy the PE tube 204 (FIG. 9). It should be realized that the PE tube can be deployed at same time and/or after the TM is penetrated, and not only after the lance is retracted. Furthermore, in some embodiments, the space in front of and/or behind the TM can be aspirated before or after deployment of the PE tube.

Figure 10:
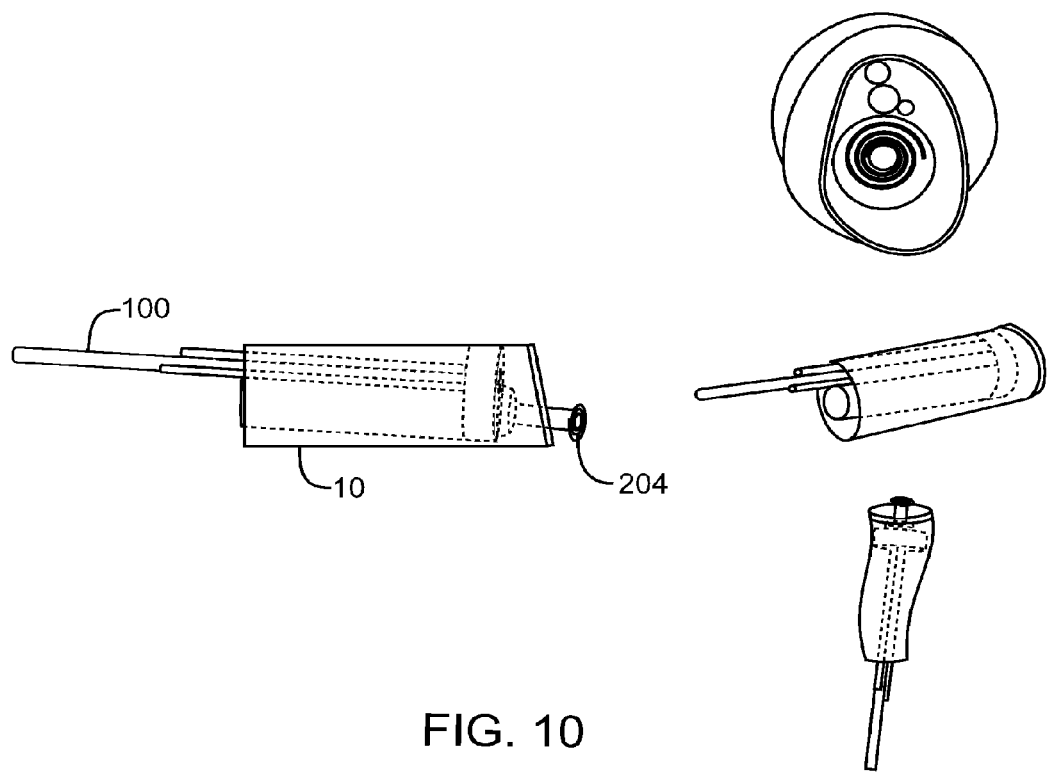
FIG. 10 illustrates the removal of the combined penetrator and delivery device.
Figure 11:
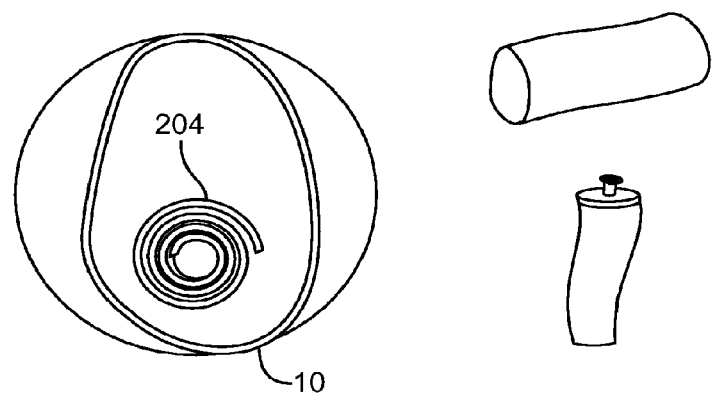
FIG. 11 illustrates the removal of the stabilizing impression.

After the delivery of the PE tube, the combined TM penetrator and delivery device 200 is removed as illustrated in FIG. 10, and thereafter the stabilizing material and the guide block are also removed, thus leaving the PE tube 204 in place in the TM, as illustrated in FIG. 11. Further details of each of these medical devices used in the above procedures are described below.

Guide Block with Targeting and Visualization Systems

FIGS. 12-17 illustrate various aspects of the guide block. The guide block in accordance with the embodiments of the present invention is configured to be inserted into the ear canal, and stabilized against the cartilaginous or bony portions of the ear canal. The guide block system can include a targeting element to ensure the combined TM penetrator and delivery device is targeted at the correct location on the tympanic membrane and to confirm the guide structure is located within a defined distance from the tympanic membrane. The guide block system can also allow the insertion of an endoscope for visualization. The guide block system can also include working channels for insertion of the iontophoresis system electrodes, the PE tube delivery device, suction, irrigation and other devices for delivery of therapeutic agents.

Figure 12:
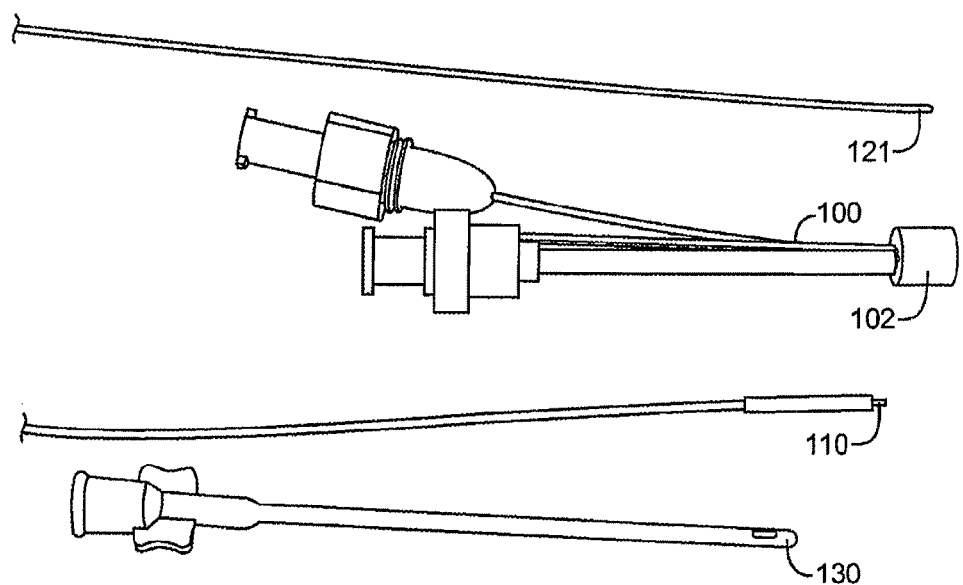
FIG. 12 illustrates an exemplary guide block system in accordance with one embodiment of the present invention.

FIG. 12 illustrates the guide block system 100 in accordance with one embodiment of the present invention. As shown in FIG. 12, the guide block 100 has a foam block 102 at its distal end. The foam block 102 can be dimensioned to have different outer diameters (e.g., at 2 mm increments from about 3 mm to about 13 mm) to fit different size ear canals of adult patients as well as pediatric patients. The foam block's thickness is selected to take up a minimum amount of axial space within the ear canal while providing enough thickness to provide a relatively secure initial placement within the ear canal, act as a dam for the impression material, and act as a dam for the Lidocaine and epinephrine and prevent the solution from exiting the ear. The foam block or disk allows for the variable positioning within the cross section of the ear canal. The foam block 102 can be compressed during the insertion of the guide block 100 to minimize patient discomfort resulting from the foam disk contacting the ear canal. The slow recovery properties of the foam allow it to stay compressed during insertion and then expand to fill the cross section of the ear canal once proper placement is attained. The foam disk 102 can then act as a dam, preventing the impression material from flowing into the space between the foam disk 102 and the TM. In addition to the closed cell foam described above, the disk 102 can be made of a soft, open cell foam. The soft open cell foam can be constricted with a sheath that can be pulled back to spring open the foam—which will act as a dam. The foam will spring quickly—unlike the "slow" release of the closed cell foam. The sheath can be a tube running the entire (or close to the) length of the guide block lumens. It can also be a short sleeve with strings or other means so that when the sleeve is pulled back, it leaves the main shaft free for adherence to the impression material. The sheath can also be "tear away" in style.

FIG. 12 also shows that the guide block system 100 is configured to cooperate with an electrode 110 for the iontophoresis module, an endoscope 121 for visualization, and a fill nozzle 130 for delivering the impression material into the ear canal.

Figures 13A, 13B:
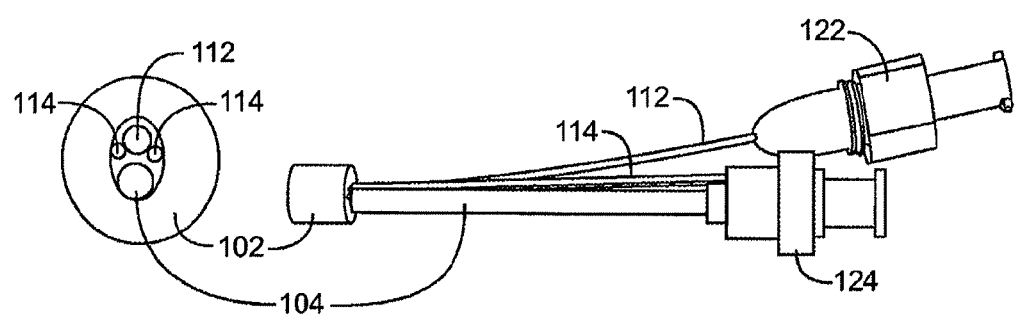
FIG. 13A illustrates further details of the guide block system of FIG. 12.
FIG. 13B is a transverse view corresponding to FIG. 13A.

FIG. 13A illustrates further details of the guide block system of FIG. 12, and FIG. 13B is a transverse view corresponding to FIG. 13A. As shown in FIGS. 13A-B, the guide block 100 includes a working channel 104, an endoscope channel 112, and one or more vent tubes 114. At the proximal end of the working channel 104, the guide block 100 includes a one way valve 124, and at the proximal end of the endoscope channel 112, the guide block 100 includes an endoscope clamp 122. The one way valve 124 allows the iontophoresis solution to be injected into the space between the distal end of the guide block 100 and the TM without the iontophoresis solution leaking back out of the working channel 104. In one embodiment, the one way valve is configured to seal around the iontophoresis electrode when it is placed in the working channel. The endoscope clamp 122 allows the endoscope to be locked in position with respect to the guide block so as to stabilize the endoscope image and free the operators one hand.

FIGS. 14A-B illustrate detailed sectional views for the guide block system of FIG. 12. FIGS. 14A-B show one exemplary arrangement for the elements of the guide block 100. FIGS. 14A-B also show that a sleeve 126 can surround the working tube 104, the vent tubes 114, and the endoscope channel 112. In addition, FIGS. 14A-B also show that an adhesive layer 128 is used to connect the sleeve 126 with the foam block 102; and that the sleeve 126 includes an adhesive layer 129 on its internal surface to help securely hold the working tube 104, the vent tubes 114, and the endoscope channel 112.

The working channel 104 can be made from a medical grade transparent plastic tubing. The working channel 104 is the conduit for the delivery of iontophoresis solution, the iontophoresis electrode, and the injection of irrigation solution. The working channel 104 is also the conduit for delivering the combined TM penetrator and delivery device 200 near the target tissue region. The working channel 104 is also the conduit for delivering the targeting apparatus near the target tissue region. The distal end of the working channel 104 can be tapered down to prevent the insertion of auxiliary devices past the distal end of the working channel so as to prevent any accidental damage to the TM. In one embodiment, the preferred length of the working channel is between 5-10 cm and preferably about 7 cm.

The endoscope channel 112 can be made from a medical grade transparent plastic tubing to allow visualization through the walls and it is sized to fit a small (i.e. 1 mm) flexible endoscope. The transparency and the resulting visualization is useful to check for voids in the impression material, bubbles in the local pain inhibitor, and align the image on the endoscope monitor with the position of the guide block. The endoscope image can be registered by use of colors or features on other guide block components.

The one or more vent tubes 114 allow air to escape as iontophoresis solution is inserted, prevent excessive pressure on the tympanic membrane during iontophoresis solution injection, and are also used to relieve any negative pressure within the ear canal as any device is removed from the ear canal. The vent tubes 114 are sized to allow relief of pressure, which can be positive during injection of iontophoresis solution and negative during the guide block removal. The vent tubes 114 are sized to allow relief of pressure with a minimum amount of resistance while maintaining a small cross sectional area so that surface tension would not allow the iontophoresis solution to leak back out of the working channel 104. The wall thickness for all the tubes and channels is chosen to ensure an adequate column strength during their insertion to be resistant to buckling or crushing, yet be strong enough to maintain flexibility and have a minimal cross sectional footprint. Ribs, bumps, or other protrusions may be added along the length of the guide block tubes and channels to help create an interlock with the impression material.

FIGS. 15A-C illustrates exemplary views seen by the endoscope of FIG. 12, when the guide block system is in place in the patient's ear. As set forth above, the endoscope image can be cross-referenced by use of colors or features on other guide block components. FIG. 15A shows the vent tubes 114 as seen by the endoscope through the transparent endoscope channel 112. The TM can also be seen. FIG. 15B shows the colored working channel 104 as seen by the endoscope through the transparent endoscope channel 112. The TM can also be seen. FIG. 15C shows an image where a stripe of color in the endoscope channel 112 can help orient the observer of the endoscope image.

Figure 16:
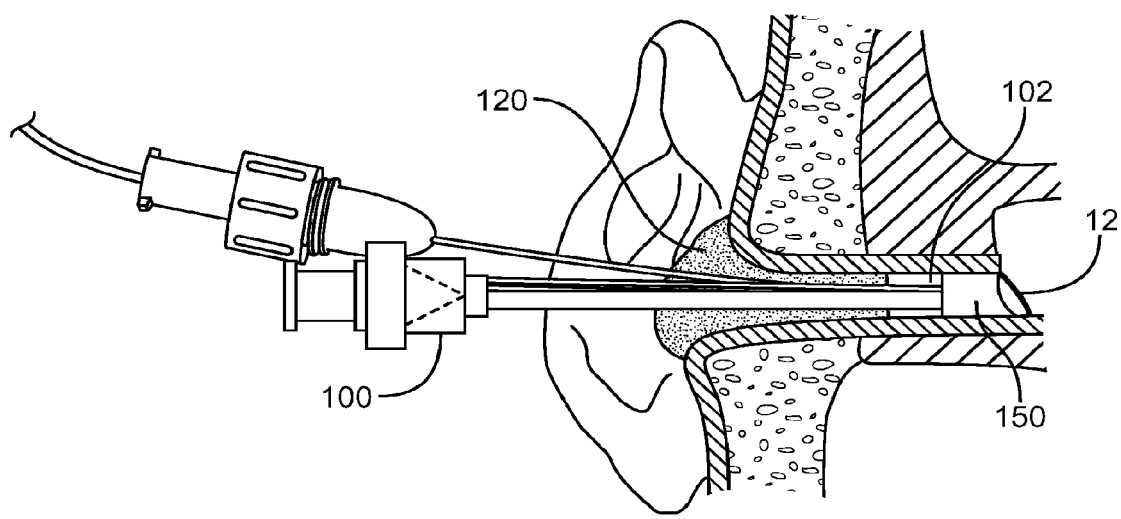
FIG. 16 illustrates an anterior sectional view of the guide block system in place in the patient's ear.

FIG. 16 illustrates an anterior sectional view of the guide block system 100 in place in the patient's ear. As is shown on FIG. 16, the guide block is in place in the right ear. Impression material 120 fills in around the guide block system to secure it in place. The foam disk 102 is placed lateral of the TM 12 and within the bony or cartilaginous structure of the ear canal. The impression material 120 is injected into the ear canal around the tubes of the guide block, filling the ear canal and extending into the concha or the outer ear. The impression material 120 helps stabilize the guide block with respect to the TM. The working space 150 between the guide block 100 and the TM 12 can be filled with the iontophoresis solution.

The fill nozzle 130 is used to deliver the impression material. The fill nozzle 130 can be placed external to or near the inside of the ear canal. The fill nozzle 130 can have a large bore and a tapered distal end, so as to ensure a complete fill of the ear canal space around the guide block by maximizing the velocity and momentum of the impression material 120 as it leaves the fill nozzle 130. Alternatively, the fill nozzle 130 can be placed deeper in the ear canal and retracted as the ear canal fills with the impression material, so as to ensure a complete fill by filling in the ear canal from next to the foam disk 102 first. The fill nozzle 130 can have one or more offset holes near its distal end that may be located on the side walls of the fill nozzle 130 in addition to or in place of an axial hole at the distal end of the nozzle. The one or more side holes for the fill nozzle 130 can improve the safety of the device since with this arrangement the impression material is not injected directly at the foam disk 102, which could lead to the leaking of the impression material past the sides of the foam disk 102. The one or more side holes for the fill nozzle 130 can help promote a complete fill by better reaching pockets or voids that could be blocked otherwise. Alternatively, more than one fill nozzle may be used to circumferentially surround the guide block to ensure a better and more complete fill. The one or more nozzles could issue from a common header or could be separate fill nozzles. There can also be a lumen in the guide block for filling. In that case, the fill nozzle can be connected to the guide block and thus could fill from the block back to the opening in the canal. This can ensure consistent filling and elimination of voids.

The fill nozzle can have depth and orientation markers to that the position of the tip hole(s) could be detected even when the tip is not visible. The depth and/or orientation markers can be placed on the proximal portion of the fill nozzle 130. The depth markers can line up with portions of the guide block to indicate that the tip of the nozzle is adjacent to the foam disk 102. Orientation markers that may be separate or combined with the depth markers can be used to indicate the orientation of the nozzle hole(s).

Figure 17C:
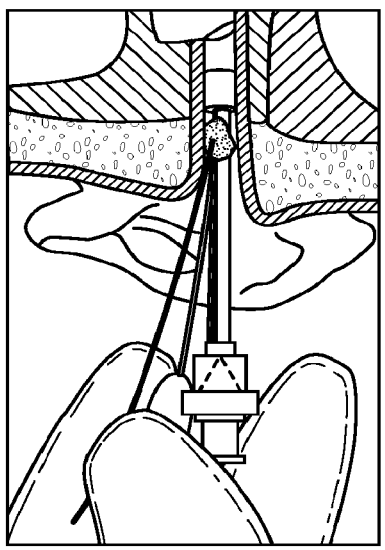
FIGS. 17A-F illustrate the deployment of the guide block system in place in the patient's ear.
Figure 17F:
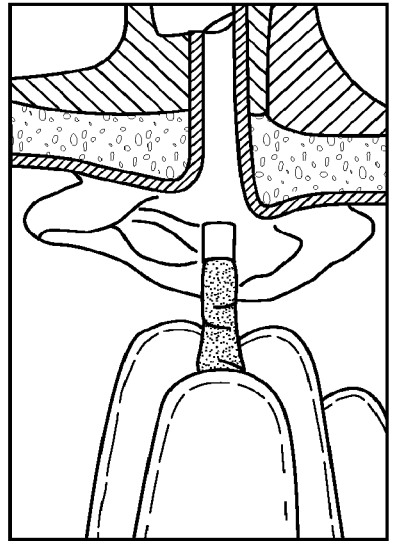
Figure 17B:
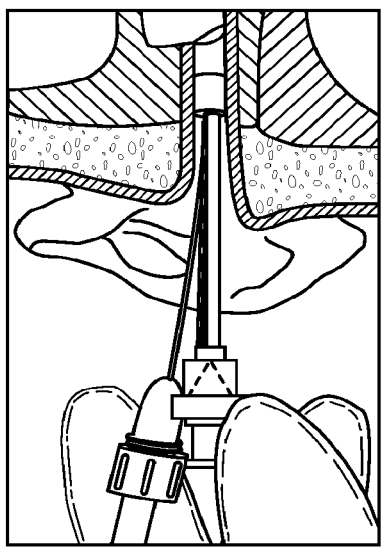
Figure 17E:
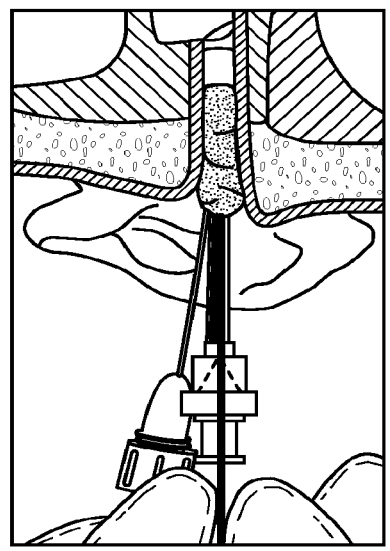
Figure 17A:
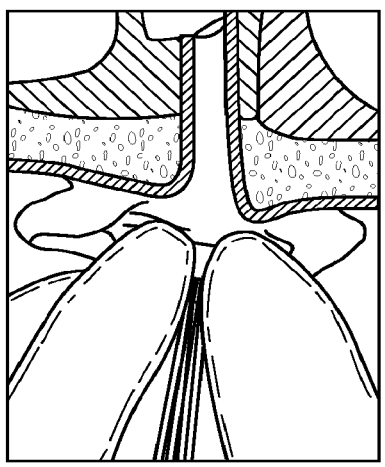
Figure 17D:
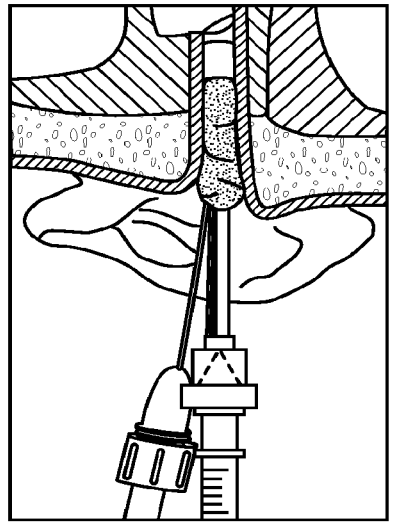

FIGS. 17A-F illustrate the deployment of the guide block system in place in the patient's ear. FIG. 17A shows that the foam disk 102 is compressed before the guide block is inserted under endoscopic visualization (FIG. 17B). Then in FIG. 17C, the ear canal is filled with the impression material. In FIG. 17D, once the impression material has hardened, a solution containing the pain inhibitor is injected into the working space. In FIG. 17E, the iontophoresis electrode is inserted to deliver the iontophoresis. Then at FIG. 17F, the guide block and the impression material are removed.

The guide block system is also configured to enable the visualization of the iontophoresis electrode(s). In order to achieve this, the tip of the iontophoresis electrode is visible via the endoscope to ensure that the electrode is in contact with the iontopheris solution and not surrounded by a bubble or air pocket which could reduce the anesthetic effect.

Figure 53:
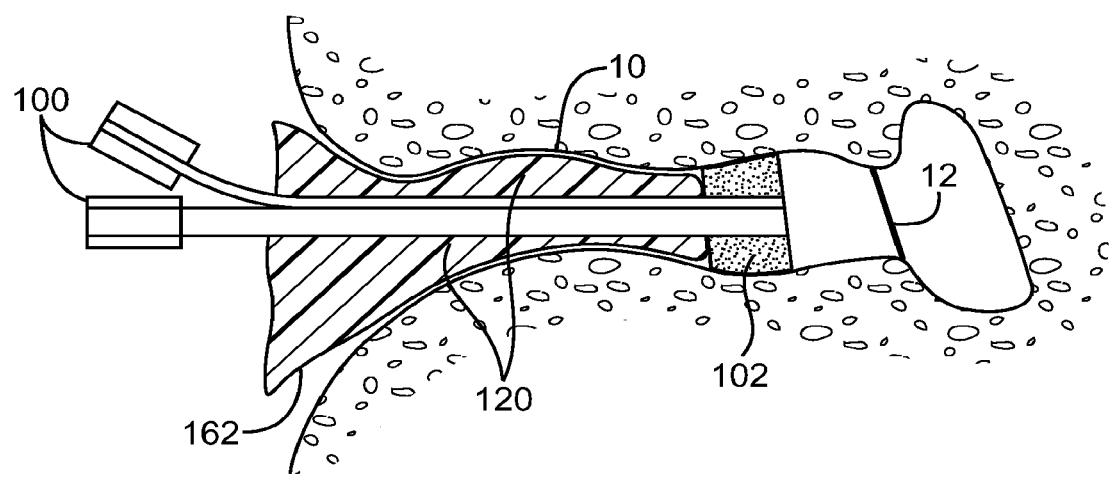
FIG. 53 depicts an embodiment where a thin polymeric barrier is attached to the distal end of the guide block.

Certain aspects of the embodiments of the present invention are directed toward features that can prevent the impression material from encroaching past the distal end of the guide block. As described above, the guide block system includes a foam disk mounted on the distal end of the guide block tubes so as to prevent the impression material form flowing into the space between the distal end of the guide block and the TM. FIG. 53 depicts an embodiment where a thin polymeric barrier is attached to the distal end of the guide block. In accordance with this embodiment of the present invention, the foam disk 102 can be augmented or even replaced by a thin polymeric barrier 162 that is attached to the distal end of the guide block 100. The thin polymeric barrier 162 is open at its proximal end, and it is configured to fit into the ear canal like a trash bag would fit in a trash can. When the impression material 120 is injected in the proximal opening of the barrier 162, it flows into the ear canal, expanding the barrier 162 against the walls of the ear canal 10. The barrier 162 will prevent the flow of the impression material 120 past the distal end of the guide block 100, since the barrier 162 is closed and attached with the guide block at its distal end. The open end of the barrier 162 can be dimensioned to be large as shown or small, such as a luer fitting. The impression material can also be injected into a compliant balloon or pouch placed on the guide block working channel or vent tubes. In this configuration, the impression material would be prevented from moving into the space between the guide block and the TM.

Various additional details for the guide block system described above are provided below. As described above, the guide block system is used in a highly variable anatomy of the ear canal to provide a stable platform for subsequent steps requiring precision and accuracy, for example for the placement of PE tubes. Accordingly, the placement and the fixation of the guide block should preferably be quick. The fixation should be secure and rigid with respect to the TM, and the guide block deployment needs to be able to fill complex, non-centric and sensitive regions in the ear canal in order to fix the guide block in place. For example, the foam disk that is used at the distal end of the guide block is compressed for a low profile during delivery to avoid contact with the sensitive ear canal wall. However the foam disk then expands to fill the space between the guide and the ear canal. The foam disk can be a memory foam. The memory foam can be a slow recovery urethane or vinyl foam similar to those used in ear plugs. The advantages of the memory foam are that it is simple, currently available, low in cost and easily producible in a range of sizes. The impression material can be a catalyzing foam. The catalyzing foam can be a two-part foam that uses the addition of two components to produce the foam which can set up rapidly in the ear canals. The advantages of the catalyzing foam are that it has a very low profile during delivery, it can fit into any shape canal and it can be formulated to have varying hardening speeds. In addition to the use of catalyzing foams to stabilize the guide block system within the ear canal, the following alternative stabilization schemes are also within the scope of the embodiments of the present invention. These alternative stabilization schemes include the use of balloons, deformable mechanical elements, and bulk material fills, and are described below.

FIGS. 46A-B illustrate the use of multiple longitudinal balloons 570 that are used to stabilize the guide block tubes within the ear canal. The use of balloons is advantageous in that the balloons have a low profile during their insertion; they are quick to set up and take down. In addition, the use of balloons enables the stabilization of the guide block in different shaped and sized ear canals. The arrangement shown in FIG. 46A-B allows for the guide block tubes to be placed offset in the ear canal via selectively shaped or inflated balloons.

FIGS. 47A-B illustrate the use of multiple circumferential balloons 572 that are used to stabilize the guide block tubes within the ear canal. The arrangement shown in FIGS. 47A-B can be used to fit the varying diameter of the ear canal along its length by expanding balloons at several locations. The advantages of this embodiment are that the balloons do not have to contact the sensitive areas of the ear canal; a range of ear canal sizes and configurations can be handled with one device; and the sequential inflation of the tubes may allow for better adjustment of the dominant axis of the guide block tubes with respect to the target location on the TM.

FIGS. 48A-B illustrate the use of a compliant balloon 574 that is used to stabilize the guide block tubes or act as a dam within the ear canal. As is shown in FIGS. 48A-B, a single balloon can expand to gently fill the entire space between the guide block tubes and the ear canal, in a manner similar to a latex compliant balloon catheter.

The balloon-based schemes for the stabilization of the guide block can have the one or more balloons filled with air, water, saline or similar material. Alternatively, the balloons can be filled with other substances for more secure anchoring by means of a more rigid balloon(s). One such filling can be a two-part reaction system, where a balloon is first filled partially with a one substance and then the second substance is added. The two substances react chemically to form a harder substance. Either of the substances can be in powder, liquid or gas form. Another such filling can be a two-part or a one-part system that reacts and expands in volume to ensure a complete fill of the ear canal volume while not placing excessive pressure on the ear canal. Another such filling can be a two-part or a one-part system where the fill is UV-activated. Additional substances may be introduced at the end of the guide block stabilization procedure to promote the removal of the expanded balloons.

FIGS. 49A-B illustrate the use of an offset balloon 576 that is used to stabilize the guide block tubes within the ear canal. As can be seen in FIGS. 49A-B, in order to allow for non-concentricity of the guide block tubes with respect to the ear canal, the balloon 576 is not concentric with the guide block tubes. The use of the non-concentric placement of the guide block tubes with respect to the balloon(s) can also be implemented with the embodiments depicted in FIGS. 47-48 above. Furthermore, the non-concentric placement of the guide block tubes with respect to the balloon(s) can also be implemented with offset hole(s) in a foam block.

As set forth above, one alternative stabilization scheme includes the use of deformable mechanical elements. The deformable mechanical elements include structural elements that are displaced so that the restorative force of the elements acts on the ear canal walls to stabilize the guide block system. The use of the deformable mechanical elements can be combined with foam or balloon-based methods described above.

Figure 50A:
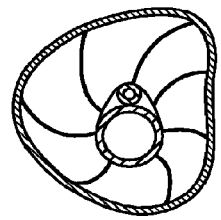
FIGS. 50A-B illustrate the use of spokes in a balloon that are used to stabilize the guide block tubes within the ear canal.
Figure 50B:
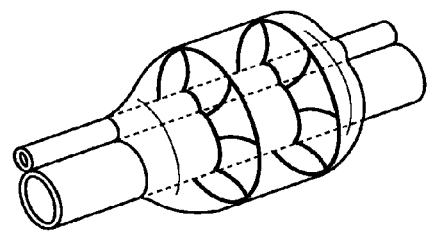

FIGS. 50A-B illustrate the use of spokes in a balloon that are used to stabilize the guide block tubes within the ear canal. As is shown in FIGS. 50A-B, malleable spokes or ribs extend between the guide block tubes and the balloon surrounding the guide block tubes such that the spokes guide the inflation of the balloon when, for example, when the balloon needs to be non-concentric with respect to the guide block tubes.

Figure 51A:
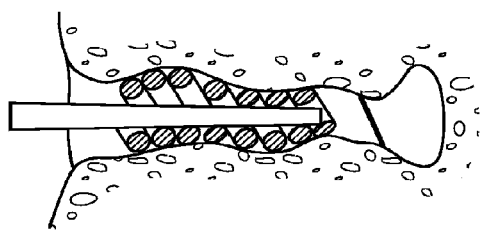
FIGS. 51A-B illustrate the use of coil springs that are used to stabilize the guide block tubes within the ear canal.
Figure 51B:
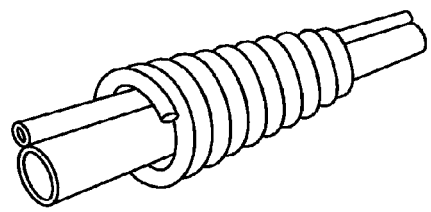

FIGS. 51A-B illustrate the use of coil springs that are used to stabilize the guide block tubes within the ear canal. As can be seen in FIGS. 51A-B, a coiled spring are dimensioned to fit in the ear canal, whereby the restorative force of the spring tries to maintain the cylindrical shape, thus stabilizing the guide block system in the ear canal.

Figure 52A:
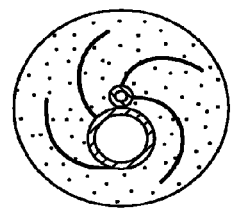
FIGS. 52A-B illustrate the use of coils in a foam that are used to stabilize the guide block tubes within the ear canal.
Figure 52B:
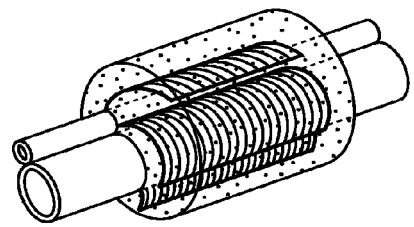

FIGS. 52A-B illustrate the use of coils in a foam that are used to stabilize the guide block tubes within the ear canal. As is depicted in FIGS. 52A-B, spring elements in the foam in the form of coil ribs aid in the expansion speed and force of the stabilizing scheme.

As set forth above, one alternative stabilization scheme includes the use of bulk material fills. As described above, one stabilization scheme involves the use of catalyzing foams to stabilize the guide block system within the ear canal. One type of catalyzing foam is a two-part vinyl polysiloxane impression material that is injected into the ear canal around the guide block tubes as a viscous material which then hardens over time to provide for the anchoring of the guide block system within the ear canal. Based on known otological methods and material, this impression-material scheme is able to fill the ear canal space with a minimal amount of pressure on the ear canal. The known methods and material can be enhanced in order to reduce patient discomfort by modifying them to increase the speed of cure or the hardness of the cure by accelerants that include the use of chemically reactant accelerants, electricity, UV and/or heat. Heat as used herein provides additional benefits, in that the warming of materials to near body temperature can be more comfortable for patient, and the lower temperature difference is less jarring on the patient. Additionally, heat can also allow the stabilization material to potentially flow faster and thus enable a better fill.

Figure 36A:
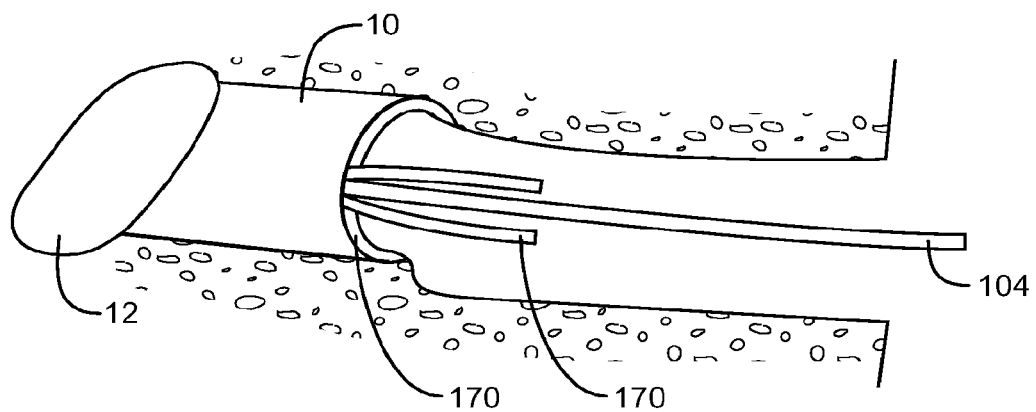
FIGS. 36A-B illustrate an embodiment of a dam for the working channels of the guide block system.
Figure 36B:
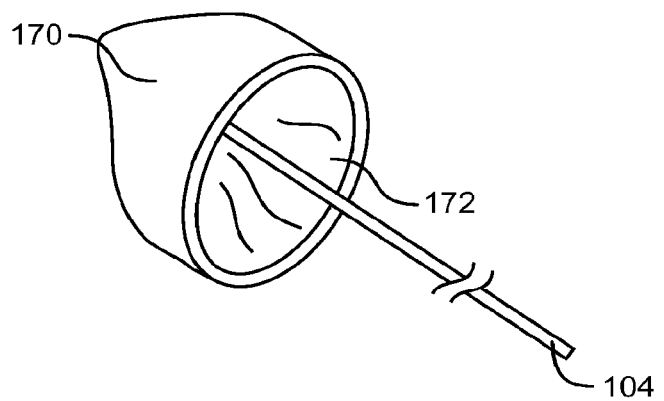

Certain aspects of the embodiments of the present invention are directed towards methods and devices for preventing or minimizing the abrasion of the ear canal while allowing for the penetration and the stabilization of the guide block within the ear canal. FIGS. 36A-B illustrate an embodiment of a dam for the working channels of the guide block system. FIG. 36A shows a portion of the working channels 104 of the guide block system 100 inside the ear canal 10, and the relative position of the distal end of the working tubes with respect to the TM 12. As can be seen, a dam structure 170 can be used at the distal end of the working channels 104. The dam structure 170 is shown in its collapsed state as it is being inserted into the ear canal 10. Once in place, the dam structure 170 is shown in its non-collapsed or deployed state. The dam structure 170 can be composed of a soft and smooth material (e.g., silicone) that is shaped to create a shroud-like structure that can be supported by a scaffold structure 172 that is internal or adjacent to the dam structure 170. The scaffold structure 172 can be deployed via actuation cables that are accessed through the working channels. In operation, using the above-described dam structure 170, the working channels 104 can be advanced into the ear canal in a "no-scrape" state and then deployed against the ear canal 10 in a radial direction, thus minimizing abrasion and discomfort to the patient. Alternatively, a delivery sheath made of a very soft material that minimizes the abrasion of the ear canal can be used to encompass and deliver the guide block system into the ear canal, in a manner similar to how a self expanding stent is deployed. The very soft material can be made from collagen.

Iontophoresis System

Figure 18:
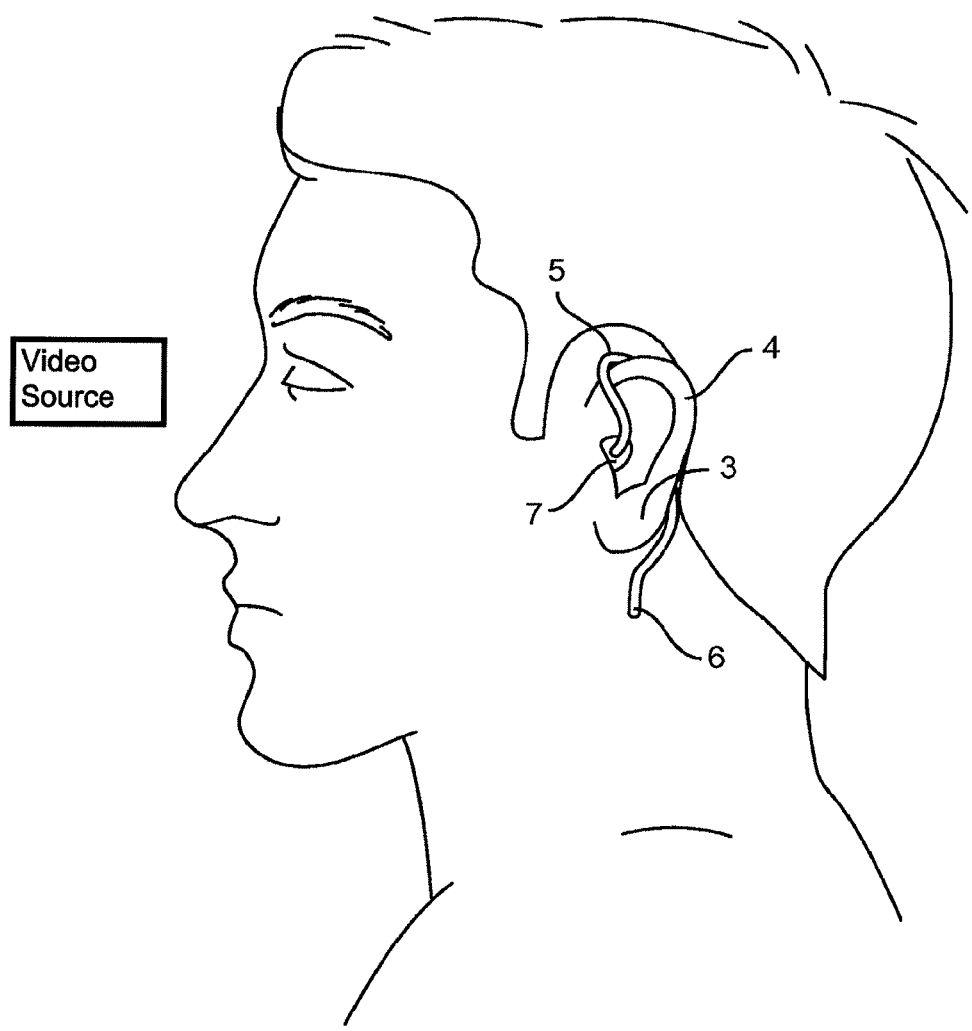
FIG. 18 illustrates an exemplary support structure that is configured to support an iontophoresis module.
Figure 18:
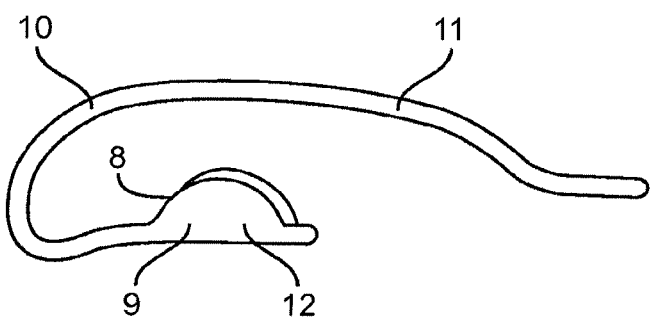

One medical device that can be supported by the support structure 1 is an iontophoresis module 4, illustrated in FIG. 18. FIG. 18 illustrates the support structure of FIG. 1 when configured to support an iontophoresis module 4. As can be seen in FIG. 18 the iontophoresis module 4 is aligned near the external ear 3, and includes a stabilizing unit and a ground electrode 5 and a battery area 6, as well as an iontophoresis unit with its associated electrodes, and ear plug and injection ports 7. The iontophoresis module 4 includes an injection port

8 and a ventilation port 9. The stabilizing electrode element can be configured to be worn around the ear. The ground electrode 11 can be worn behind the ear and can stay in alignment by use of biocompatible adhesive. The ear piece portion 12 can be configured to sit in the opening of the ear canal and close the canal and enable fluid injection and venting. The electrode wire can be formed or annealed to a predetermined shape to fit comfortably around the ear of the patient similar to miniature ear phones used with cell phones and other electronic devices.

Figure 19:
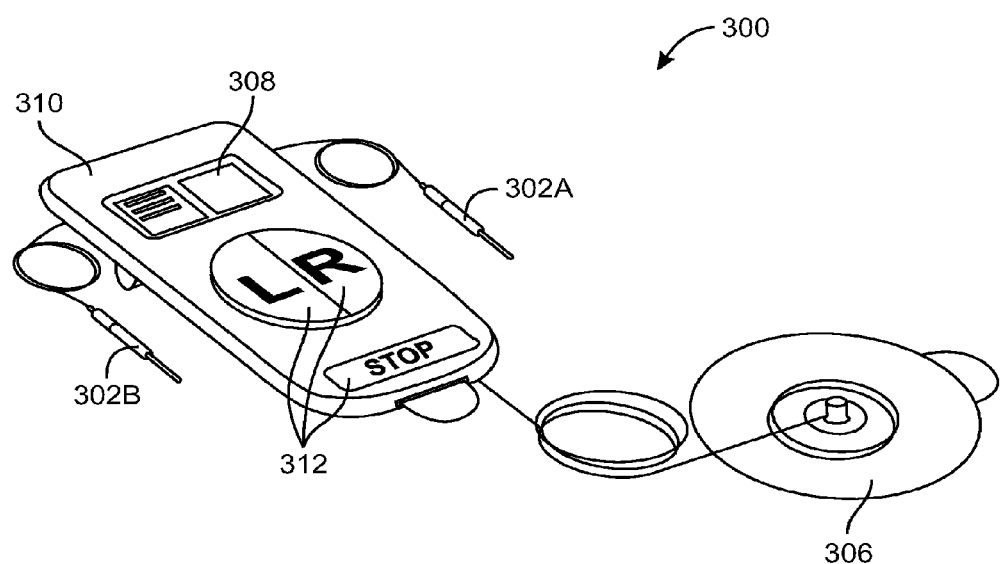
FIG. 19 illustrates an exemplary iontophoresis module in accordance with the embodiments of the present invention.
Figure 20:
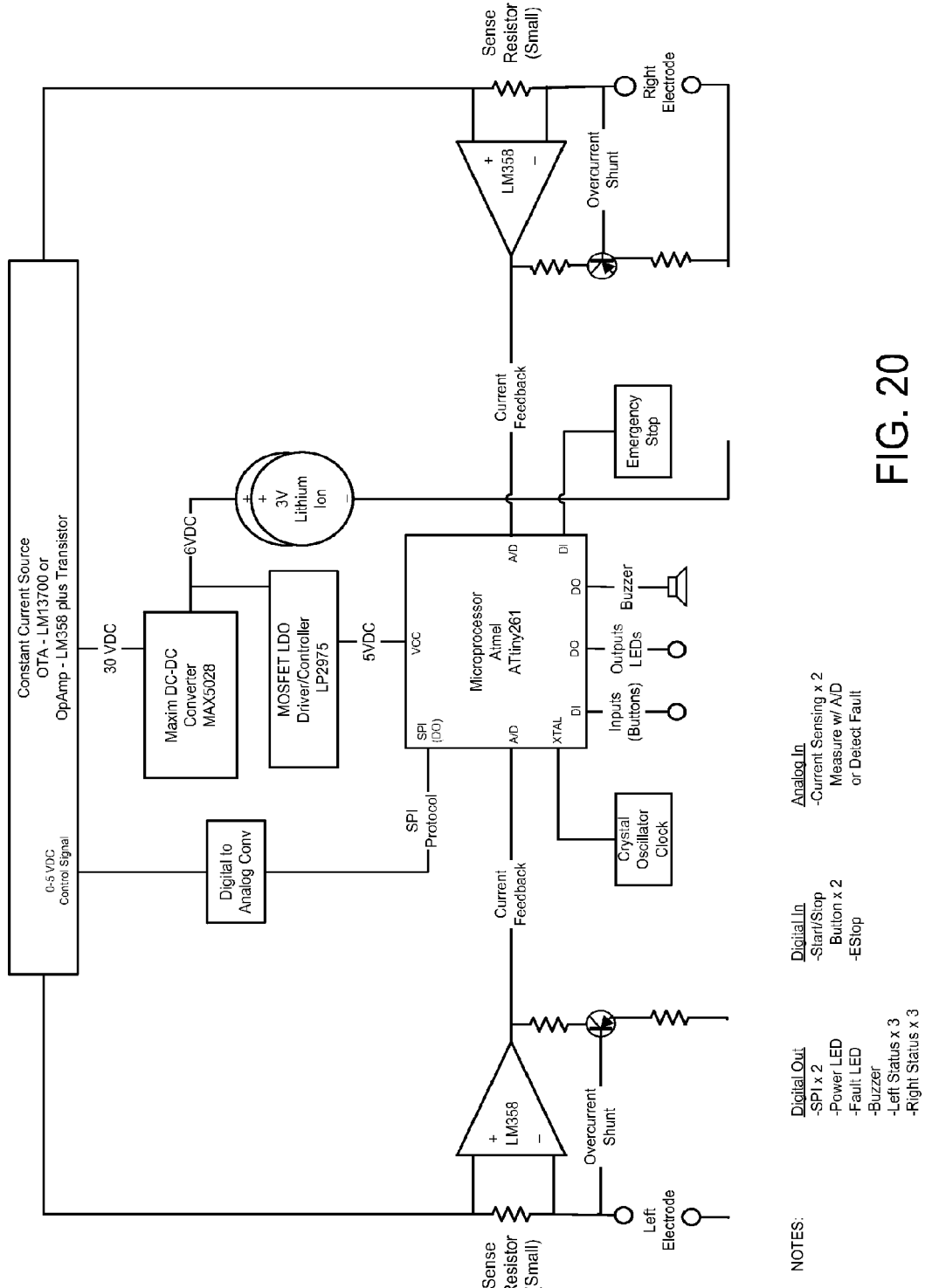
FIG. 20 is an exemplary circuit diagram illustrating the electronic architecture of the iontophoresis module of FIG. 19.

FIGS. 19-20 are used to illustrate various aspects of the iontophoresis module. As shown in FIG. 19, the iontophoresis module 300 in accordance with one embodiment of the present invention can be a battery powered disposable electronic device 310 that provides regulated current to two electrodes (one for each ear) 302A-B with a single return electrode patch 306. The electrodes 302A-B are configured to fit within the guide block one electrode for each guide block. The regulated current is used for the iontophoresis process, which applies local anesthesia or other therapeutic compounds to the tympanic membrane. As shown in FIG. 19, the iontophoresis module 300 can be a small electronic device, about the size of a business card, with a LCD display 308 and several buttons 312 for operation. Furthermore, the iontophoresis module can be co-located with the return electrode patch to minimize the amount of loose wires and overall package size. In this embodiment, the return electrode patch would be permanently or by means of a metal snap or other electrically conductive attachment mechanism attached to the iontophoresis module, and the entire assembly then adhered to the patient's skin (e.g. at the back of the neck) via the return electrode patch, thereby fixing the iontophoresis module in a location easily accessible to the physician but not easily accessible to the patient.

Figure 45:
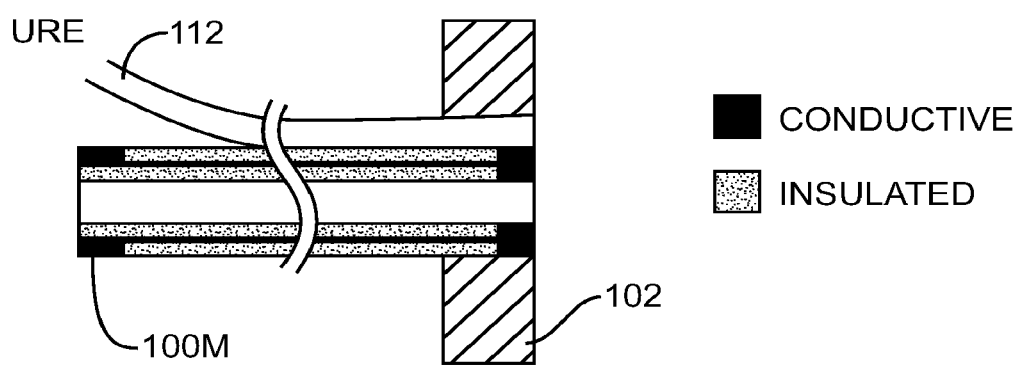
FIG. 45 illustrates an embodiment that combines the iontophoresis module's electrode with the working channel or the vent tube of the guide block system.

FIG. 45 illustrates an embodiment that combines the iontophoresis module's electrode with the working channel or the vent tube of the guide block system. As is shown in FIG. 45, the tube 104M has conductive regions at its tip and tail, and is insulated in between. This configuration of combining the iontophoresis module's electrode with the working channel or the vent tube of the guide block system can eliminate the need to deliver a separate electrode through the working channel or the vent tubes, thus speeding up the procedure.

The operation of the iontophoresis module 300 is described below. The user can turn on the iontophoresis module by pulling on a small plastic tab from the back of the unit. This tab is designed to keep the batteries from powering the circuitry until desired. Upon pulling the tab the batteries will begin powering the circuitry and the LCD 308 will illuminate. Next, the user can clip the unit to the back of the patient's collar via the clip on the back of the housing. Once the housing is set, the return electrode patch can be placed on the back of the neck. The next step is to apply the anesthesia solution into the patient's ear and position the electrode. Once completed on one side, this side can be activated independently of the other ear. If, for example, the left electrode is placed first, the user will press the "Left Ear Start" button on the main unit to begin the automatic pre-programmed current delivery sequence, starting with a current ramp-up from zero. Meanwhile, the user can place the right ear electrode into the patient's right guide tube. Once properly placed, the user can press the "Right Ear Start" button to independently begin current delivery to the right ear. A progress meter can be displayed for each ear on the LCD 308. The progress meter is represented by the filled in area of a box, that starts empty and fills in as the charge is delivered until is it fully filled and the process is complete. Once current delivery starts, the user waits for the device to signal it is finished or there is a problem via an auditory beep sound. After the device delivers the full dosage of current to each ear, the progress meter for each ear is filled and the system can deliver a short series of three beeps to signal successful completion. Once the device signals it is completed it can automatically shut down. At this point, the user can remove the electrodes, and can start the process of removing the excess lidocaine and cleaning the area. Again, this can be done independently on one side without affecting proper device operation on the other side.

At any time during the process the current delivered to an electrode can be paused by pressing the left or right button. The system will ramp down the current to that electrode. The user can also pause both electrodes at once by pressing the stop button. This will cause the system to ramp down the current to both electrodes. In either case the user can continue with the procedure by pressing the left or right buttons. This will cause the system to ramp up the current for that electrode and continue delivering the total charge where it left off before being paused. At the end of the iontophoresis current delivery cycle, the current will ramp down to zero. Once both sides have completed iontophoresis and the electrodes have been removed, the return patch can also be removed and the entire unit discarded. Power can automatically shut off after one hour of time, or any selected unit of time. The unit is designed to allow only one use and can not be turned back on. Another embodiment disables the current delivery function after a single use, but then enables additional functionality, such as a game, a clock, etc. for the patient's use after the procedure. If there is an error the system can emit a series of long beeps continuously. Alternatively, or in addition to the series of long beeps, visual means can be used, so as not to disturb the patient. For example, a blinking light located on the back of the unit or other hard to reach place would likely not be noticed by patient. Conditions that could cause such an error include: a detected open circuit or an over current condition. In the case of an open circuit, the device will automatically stop delivering current to the patient through a controlled current ramp down and the user can resume delivery by pressing the appropriate start button. In the case of over current, the device has detected an internal error, will automatically stop all current to both electrodes, will not restart, and the device should be discarded. For both cases an appropriate message is displayed on the LCD screen 308.

FIG. 20 is an exemplary circuit diagram illustrating one electronic architecture for the iontophoresis module of FIG. 19. Once the plastic tab is removed from the back of the unit, the two 3V batteries immediately begin to power the circuit. The battery supplies the LP2975 voltage regulator which delivers a very stable 5V output. The 5V output is used to supply the microprocessor (e.g., Atmel ATtiny 261), the digital-to-analog converter (DAC) converter (e.g., Maxim MCP4922), the current sensing operational amplifiers (e.g., LM358), and all components of the operator interface (buttons, buzzer, LCD). The microprocessor controls the majority of the functions of the emergency stop button to ramp down current to both electrodes;—analog inputs for sensing current delivered to each electrode; serial peripheral interface (SPI) communications to set reference for the DAC; control signals for buzzer and LCD. External to the microprocessor, the 6V battery power drives the MAX5028 DC-DC converter which converts the battery voltage to a 30V output. This output is used as the rail power for the constant current unit. The constant current unit can be designed using one of two alternatives. The first alternative uses an Operational Amplifier (Op-Amp) such as LM358 which converts a differential input voltage (the control signal) to an output voltage, and eventually to a current based on the chosen sense resistor. The second technique uses Operational Transconductance Amplifiers (OTA) which operate in a manner similar to an Op-Amp in that it is controlled by a differential input voltage, but it drives an output current based on a biasing current provided externally.

The microprocessor sets a reference voltage level to the current source using a DAC. The microprocessor communicates to the DAC via a serial protocol SPI. The constant current source uses a control signal (0-5V) from the microprocessor to ramp 0 to 1 mA of current according to a predetermined ramp shape. The DC-DC converter provides a high enough rail voltage (30V) to allow the constant current source to drive 1 mA of current based on a maximum expected body resistance of 22.5 kOhms. The body resistance is based on research performed by the assignee herein. After the allotted delivery time the microprocessor ramps the control signal back down to 0V which reduces the current delivered by the current source back to zero.

The system uses an LM358 Op-Amp on each electrode line to measure the current delivered to the patient. The Op-Amps are connected to analog-to-digital converters internal to the microprocessor. This gives feedback information to the microprocessor for sensing of open circuits within the electrode circuit and to calculate total charge delivered to the patient. For safety, the current sensing Op-Amps in parallel with the output electrode also drive an over current monitor. If a fault occurs and current increases beyond a set limit of 1.5 mA due to some internal failure, the transistor in the over current shunt will open and allow the increased current to bypass the load, the patient in this case, and safely return to the cathode (negative terminal) of the battery. The microprocessor will independently detect the over current condition, shut down the current source, and inform the operator of a system fault.

After the system has completed delivering the total charge to the patient it goes into a finished state and begins a timeout count. At the end of the timeout count the firmware turns off the system and cannot be turned back on. The microprocessor includes EEPROM memory that is written to when the system is turned on initially. If the system is re-powered, for instance, by forcibly replacing the batteries, the firmware will detect that it has been powered before and will not turn on again. This scheme is to ensure the device is one time use only. The microprocessor includes internal brown out detection to detect if the system voltage is below nominal This detection is used by the firmware to disallow the system to begin or complete operation if the system does not have enough power (e.g. if the batteries are drained).

Another embodiment of the iontophoresis device combines the iontophoresis activation with the delivery of the anesthetic solution. Such an embodiment includes a syringe-like device that delivers the anesthetic solution and is coupled with an iontophoresis activation mechanism such that the iontophoresis is actuated upon complete delivery of the anesthetic solution.

Certain aspects of the embodiments of the present invention are directed toward novel uses for the iontophoresis module. In accordance with one embodiment, the iontophoresis module can become a game or a clock after its single use. As described above, the iontophoresis module can be designed for single patient use, such that after it has delivered therapeutic current to one or both ears, the current-producing capabilities can be disabled. However, the device can retain battery power that would allow it to power additional functionality. For example, after a single use, the current producing capabilities are disabled and a clock feature can be enabled. The patient can take the unit home and use it as a clock. Additional functionality could also include an interactive game, that incorporates the use of the control buttons and feedback via the display screen. Physicians could start the patient playing the game, distracting the patient from subsequent procedural steps. The patient could then take the game device home, thus building a positive perception of the experience.

Certain aspects of the embodiments of the present invention are directed toward the geometry of the iontophoresis modules electrodes. In particular one aspect of the embodiments of the present invention is related to the distance the electrode is protruding beyond the distal end of the guide block into the distance between the distal end of the guide block and the TM. The results of test show that when the endoscope is flush with the end of the guide block, and the electrode protrusion is 2 mm, the edge of the electrode tip is barely visible in the endoscope image; when the electrode protrusion is 3 mm, its tip is visible; when the electrode protrusion is 4 mm, its tip is easily seen and when the electrode protrusion is 7 mm, the electrode appears to be almost at the center of the endoscope image. Accordingly, it is preferred to have the electrode tip protrude beyond the distal end of the guide block by about 4-6 mm. In addition, it is preferred that the electrode ends be symmetric to avoid operational errors if the electrode is connected backward.

Combined TM Penetrator and PE Tube Delivery Device (PETDD)

The PETDD provides a system for cutting the tympanic membrane and placing a PE tube inside the incision. The delivery device is configured to fit within the guide block system and is compatible with the PE tube design. The portion of the device that is inserted in the guide block system (including the cutting surface) can be disposable. The drive mechanism and its controls can be durable or disposable. The drive mechanism and its controls are configured to control the speed and motion of actuation to minimize sound and or sensation on the TM and to the patient. For example, a low speed drive and actuation may have a low frequency motion of the TM and thus cause a low sensation to patient. In addition, the presence of fluid or gel in space against TM may also help dampen any vibration against the TM. The penetrator device can also be configured to include suction in the device. For example, suction capability provided through a needle can enable suction at same time as tube placement to remove fluid behind the TM. Suction may also offer a more stable TM for piercing with the actuator.

Figure 21:
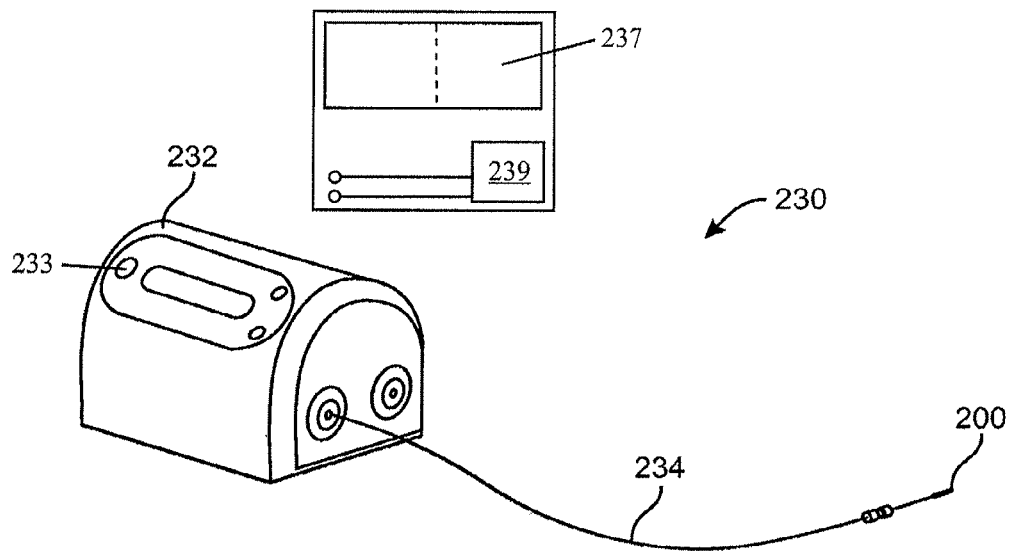
FIGS. 21-22 illustrate an exemplary conceptual design for the combined penetrator and delivery device—Combined PE Tube Delivery Device (PETDD).
Figure 22:
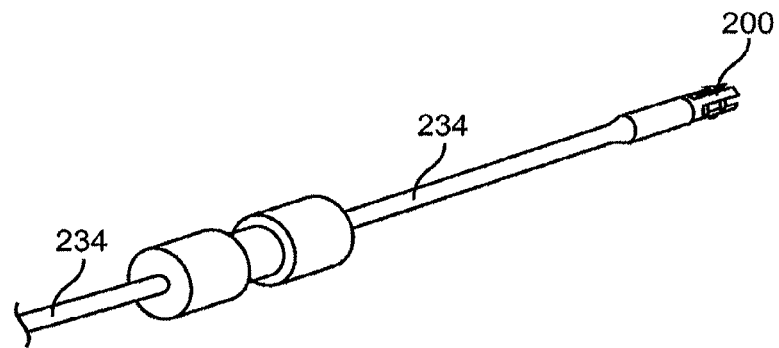

FIGS. 21-22 show an exemplary conceptual design for the PETDD 230. In one embodiment, the PETDD 230 includes two small mechanical actuator devices 200 that can cut the TM and place the PE tube within the cut. The mechanical actuators can be driven by an external linear actuator 232 through a flexible coupling 234.

As one alternative, the external linear actuator 232-234 can be a separate, durable device that can be hung on the back of the examination room chair or placed on a counter next to the endoscope equipment. The mechanical actuators are preferably sterile, disposable devices with the PE tubes preinstalled.

In operation, once the iontophoresis process is complete, the user will remove the iontophoresis electrodes and drain the ears of all lidocaine. Optionally, the guide block system can be used to rinse out the space and clean out the lidocaine with saline or water so as to remove traces of lidocaine. The rinsing or cleaning can prevent or minimize the undesirable sending of the anesthetics into the middle ear and even possibly into the inner ear. The user will then remove the PETDD actuators 200 (and attached cables 234) from their sterile packaging. The user will insert one PETDD actuator 200 into the working channel of the guide block system. While watching the endoscope display, the user will insert the PETDD actuator 200 until it is within range of contact with the TM. The user will continue to push on the actuator 200 until it hits a stop on the guide device. The piece near the TM will move relative to the rest of the actuator, so that it does not puncture the TM. Once the actuator is in place, the user can lock the actuator (e.g., by using a twisting motion). Once locked, a range finding piece will be locked to the actuator housing and the guide device. The user will then repeat the same process with the other ear. Once the PETDD actuators 200 are inserted in both ears, the user will connect the cable ends of each actuator 200 into the drive unit, i.e. controller, 232. The user will then confirm proper positioning of both PETDD actuators using the endoscope, which may be coupled to a display system 237 with a processor 239 capable of simultaneously displaying the captured image of each endoscope aligned with the treatment surface of a device, such as the PETDD, to simultaneously display the target tissue in each ear. Once positioning is confirmed, the user will press the actuation button on the drive unit. The input command delivered by the user will send a signal to the drive unit and the drive unit will provide simultaneous linear actuation of both PETDD actuators. The controller, in response to the input command, may also be configured to synchronize the simultaneous therapeutic remodeling with an audio source (See FIG. 1) and/or with a video source (See FIG. 18). The actuators can then cut the TM, and optionally also insert the PE tubes and then retract the cutting tools while leaving the PE tubes in place. The drive unit will indicate that the placement is complete. The user will then remove the guide block system from each ear and inspect the results.

In one embodiment of the PETDD and its related drive system, the drive and motion coupling functions are included in an external, durable device 232 and the range finding, cutting, and placement functions are included in a device that fits within the guide block system. As used herein, the component that fit within the guide block is called the actuator system. The external device is called the drive system.

One exemplary PETDD and its related drive system can have the following components, namely: a drive—a component that provides the basic motion to the device, and which can be external to the ear canal; a motion coupling—a component that transfers the motion from the drive to the motion for the device in the ear; if necessary, the component can also convert the type of motion provided by the drive to the motion required for actuation (i.e. convert rotary motion to linear motion); the range finder—a component that provides a means to verify that the delivery device is within the designed range of the TM; this component may or may not contact the TM; a cutting tool—a component that makes the designed incision in the TM in which the PE tube is placed; and a tube delivery—a component or assembly of components that deploys the PE tube and securely places it in the cut.

Actuator System

Figure 23:
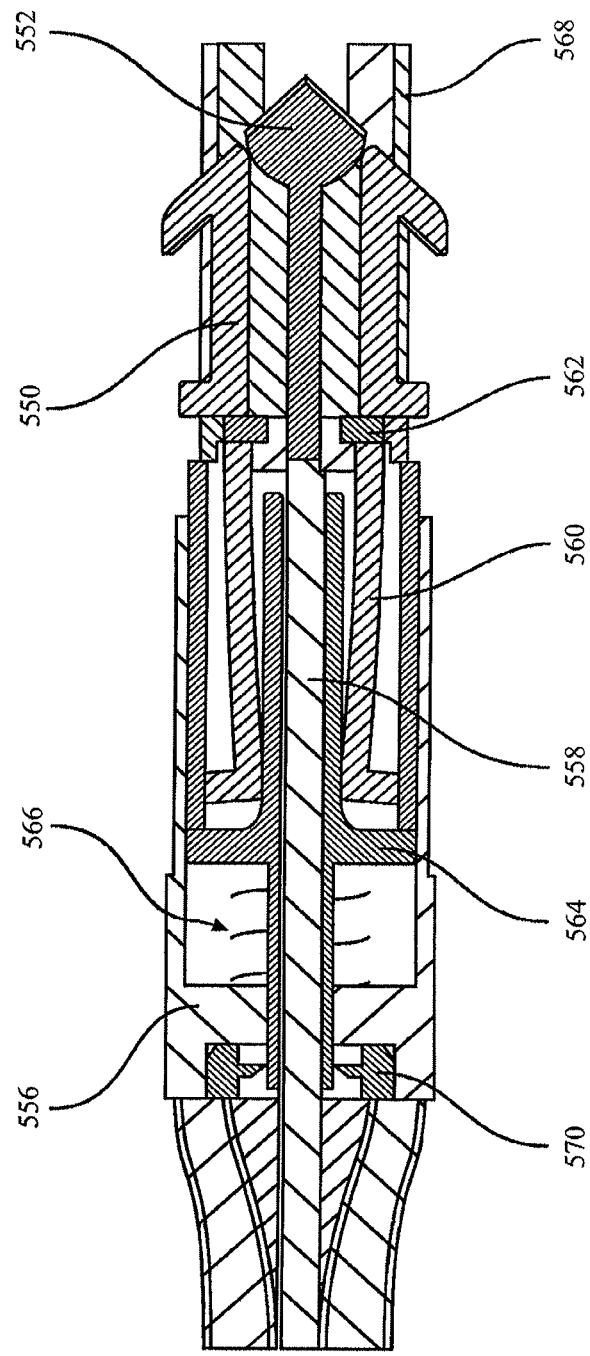
FIGS. 23-27 illustrate one embodiment of the actuator system for the combined penetrator and delivery device—Combined PE Tube Delivery Device (PETDD).

The Actuator can be mechanical, hydraulic, pneumatic, or electro-mechanical in nature. FIGS. 23-27 illustrate one embodiment of an exemplary actuation system 200. As shown in FIG. 23, the actuation system includes a PE tube 550 that rides on the outside of a cutting tool 552. The cutting tool 552 can make an incision and then the PE tube 550 is pushed through the incision until the internal (distal) flange is in the middle ear space. The cutting tool 552 is then retracted and the PE tube 550 is left in place. The PE tube 550 internal flange is shaped at an angle to help open the incision as it passes through. The entire actuator housing 556 is designed to sit within the guide block's working channel, which is inserted and stabilized within the ear canal. In one embodiment, the housing has an axial length less than 15 mm and a maximum transverse dimension of less than 5 mm.

Figure 24:
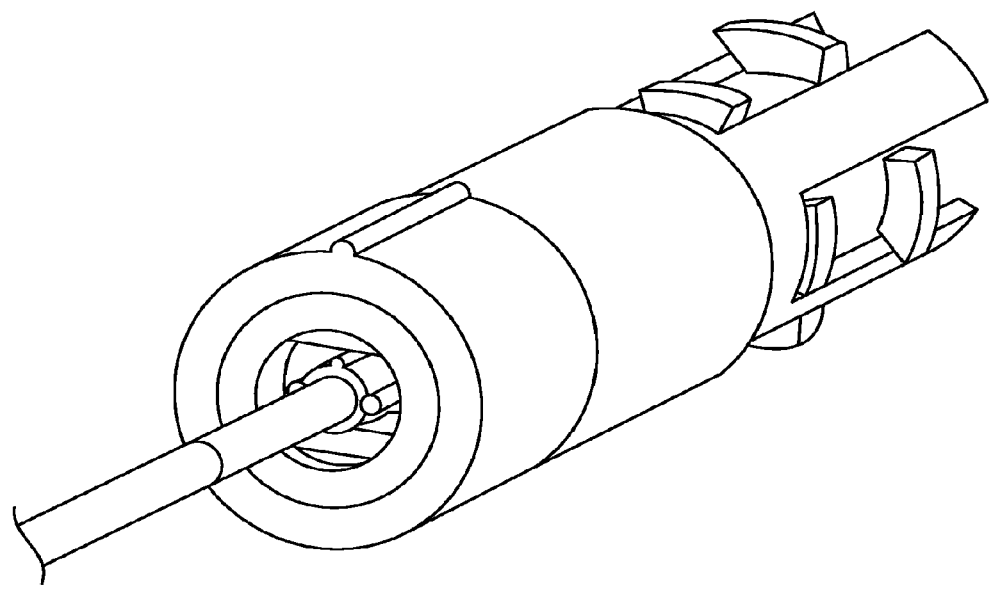
Figure 25:
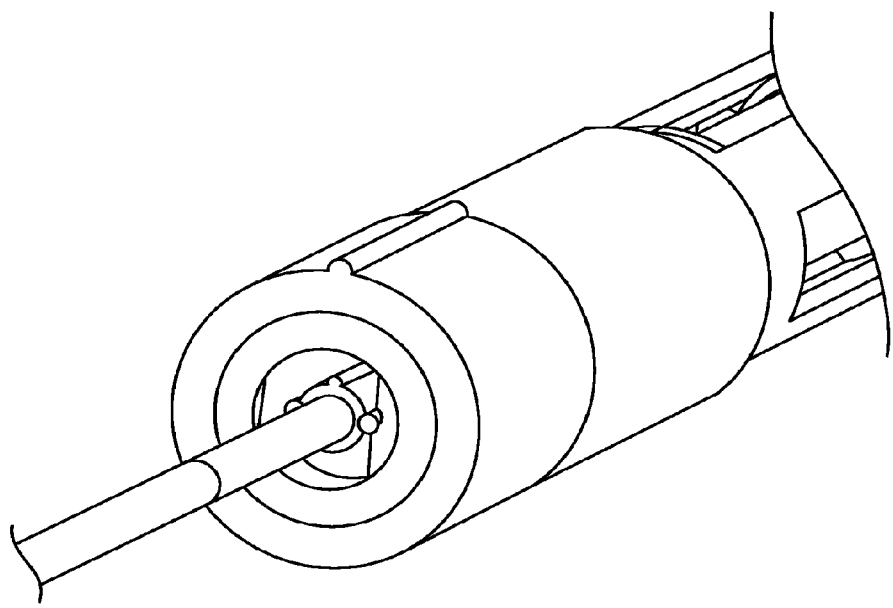

Certain components shown in FIG. 23 are also used to implement the range finding capability of the actuator system. In one embodiment, the actuator system uses a passive range finding technique. The so-called contact piece 564 contains the cutting tool 552 and the PE tube 550 and rides within the actuator housing 556. A low force spring 566 is used to put a small preload on the contact sheath 568. As the user slides the actuator unit into the working channel of the guide block, the contact sheath 568 contacts the TM and compresses the spring 566 until the guide piece is firmly seated on the hard stop in the guide device. At this point, the contact sheath 568 is touching the TM and the cutting tool 552 is a fixed distance from the end of the contact piece 564, and therefore, the TM. The spring 566 is designed so that the force applied to the TM will not cause any damage or discomfort to the patient. At this point, the contact piece 564, cutting tool 552, and PE tube 550 need to be locked to the guide piece. The locking piece, shown in FIG. 23, provides the locking mechanism. FIG. 24 illustrates the exemplary actuator in the un-locked state. FIG. 25 shows the actuator in the locked state. The locking piece 570 contains two blade-like elements that, when rotated, cut into an elastomer element on the contact piece 564, locking the contact piece in the axial direction. Once locked, the cutting plunger 558, cutting tool 552, snap piece 560, and PE tube 550 move independently from the contact piece 564 and the guide piece. The actuator is now ready to cut and deploy.

Figure 26:
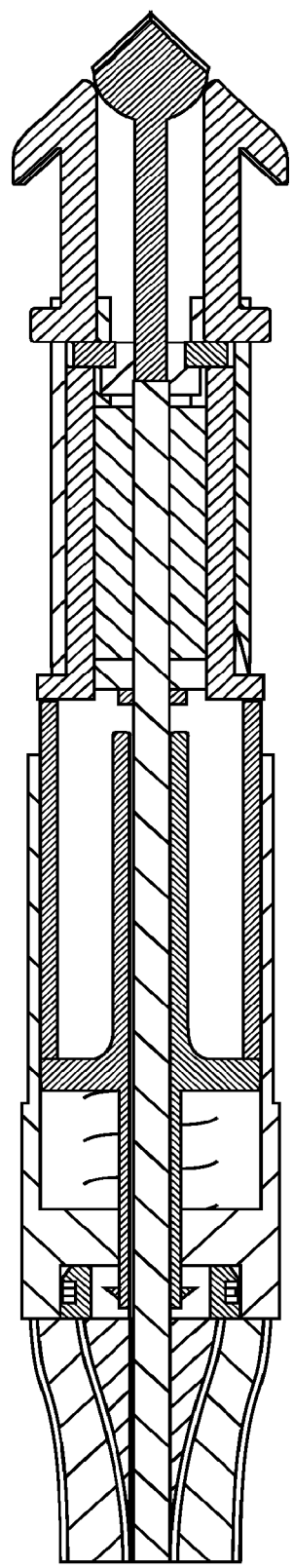
Figure 27:
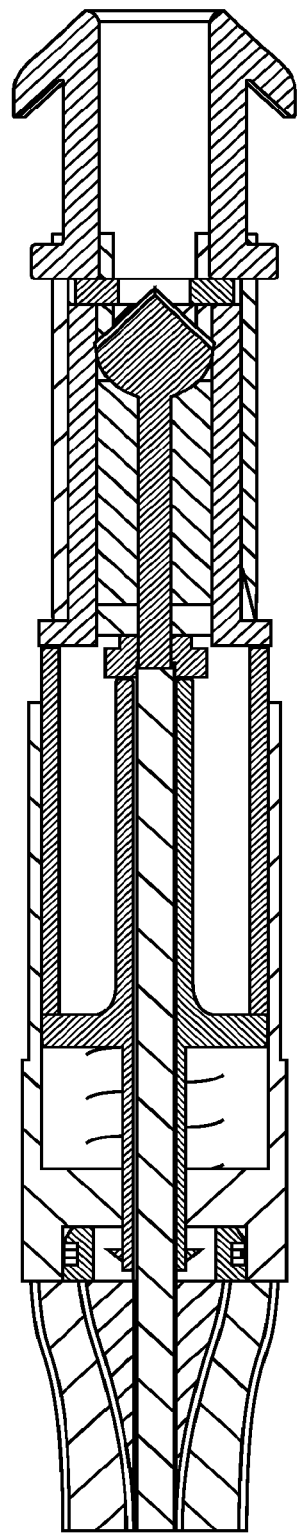

FIG. 26 shows the actuator device fully deployed, with the cutting tool 552 against a hard stop 562 created between the snap piece 560 and the contact piece 564. The snap piece 560 has two "legs" that snap out and create a locking mechanism so the snap piece is not retracted when the cutting tool 552 is retracted. FIG. 27 shows the actuator device with the cutting tool 552 retracted after PE tube 550 deployment. The snap piece 560 keeps the PE tube 550 from pulling back with the cutting tool 552, leaving the PE tube properly placed in the TM incision. At this point, the actuator or the entire guide device can be safely removed from the ear.

Motion is applied to the actuator using a cable within a sleeve. Two sleeves are used: an inner sleeve to provide the twisting motion needed to lock the contact piece and an outer sleeve to provide structural support.

The exemplary cutting tool geometry is shown as a simple, spear-like cutting tool, similar to a myringotomy spear. Other cutting tool geometries may also be used. One preferred cutting tool in the form of a myringotomy spear was found to have very good cutting characteristics, including a low cutting force, clean cut, and not impacted significantly by TM angle, TM size, and cutting speed. Other types of cutting geometries, such as spinal needles and trocar needles can create flaps after cutting through a membrane. These flaps can increase the potential for skin cells to enter the middle ear space; however potential benefits of these forms include providing increased open area through which the PE tube can be inserted, thereby reducing the amount of force exerted on the tympanic membrane and thus reducing sensation for the patient (as shown in FIGS. 38-40). The cutting tool may be actuated such that the myringotomy is specifically oriented relative to the structures of the tympanic membrane, for example in a radial or transverse direction.

Figure 40A:
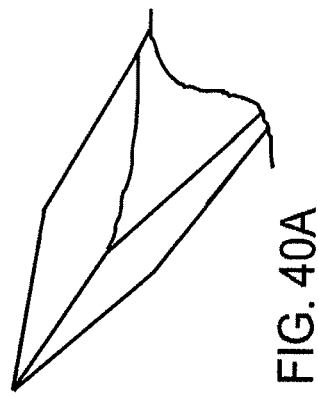
FIG. 40B shows a wye pattern hole having flaps formed in the TM by using the trocar shown in FIG. 40A.
Figure 40B:
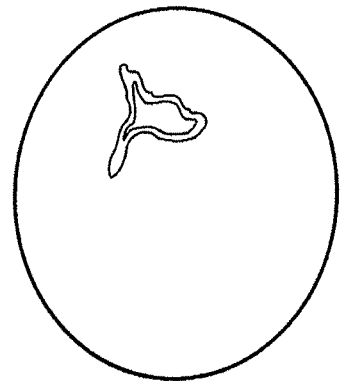
Figure 39A:
FIG. 39B illustrates a straight hole without flaps formed in the TM by using the myringotomy spear shown in FIG. 39A.
Figure 39B:
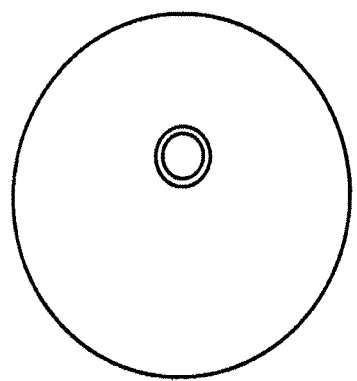
Figure 38A:
FIG. 38B illustrates a curved hole without flaps formed in the TM by using the hypo needle shown in FIG. 38A.
Figure 38B:
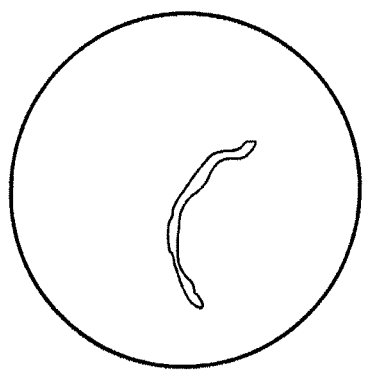

FIGS. 38-40 illustrate various myringotomy/tympanostomy hole shapes that can be made in the TM using various different cutting tools. FIG. 38B shows a curved hole without flaps formed in the TM by using the hypo needle shown in FIG. 38A. FIG. 39B shows a straight hole without flaps formed in the TM by using the myringotomy spear shown in FIG. 39A. FIG. 40B shows a wye pattern hole having flaps formed in the TM by using the trocar shown in FIG. 40A.

An exemplary drive system can include the following components: a DC motor drive; reduction gearing driving two lead screws, one for each actuator unit; a connector to covert linear motion of the lead screw to linear motion of the motion coupler between the drive system and the actuator units; an AC inlet power module and AC-DC power supply; a printed circuit board (PCB) with control electronics; an enclosure with suitable user interface and possible mounting bracket to hang on back of examination chair.

Other drive system mechanisms are possible, including concepts that can be "mounted" in a "headphone" system external to the ear and remote, handheld, manually operated mechanisms.

Figure 28:
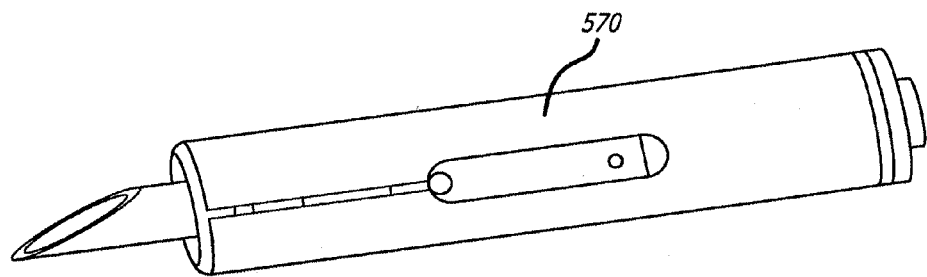
FIGS. 28-32 illustrate an alternative embodiment for the Combined PE Tube Delivery Device (PETDD).

FIGS. 28-32 illustrate an alternative embodiment for the actuation system for the combined PE Tube Delivery Device (PETDD). As shown in FIG. 28, the PETDD has a generally cylinder-shaped body that that can fit within the working channel of the guide block. The PETDD can include two actuator stages contained within the device body, one for piercing the TM and a second one for retracting the needle and deploying the PE tube. Electrical connections to the actuator can be made to wire elements for the pierce and retract stages. Four wires can be used for the actuator of FIG. 28 which can terminate at a flex circuit.

Figure 29:
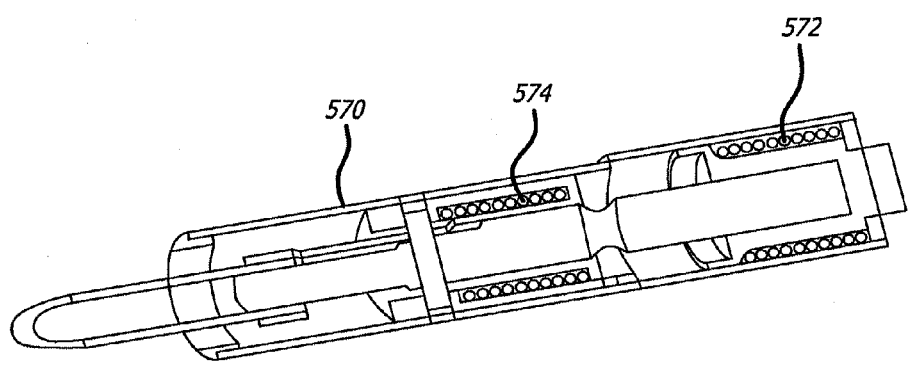

FIG. 29 shows a sectional view through the centerline of the PETDD of FIG. 28. As is shown in FIG. 28, the PETDD can have a stainless steel housing 570. The housing 570 surrounds a pierce actuator spring 572 and a retract actuator spring 574. The piece actuator spring 572 is held in a compressed form by a pierce wire fuse. The retract actuator 574 is also held in a compressed form by a retract wire fuse. The operation of the PETDD is described in conjunction with FIGS. 30-32.

Figure 30:
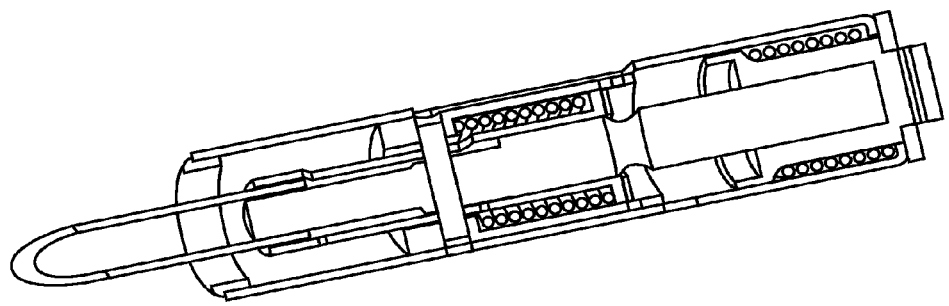
Figure 31:
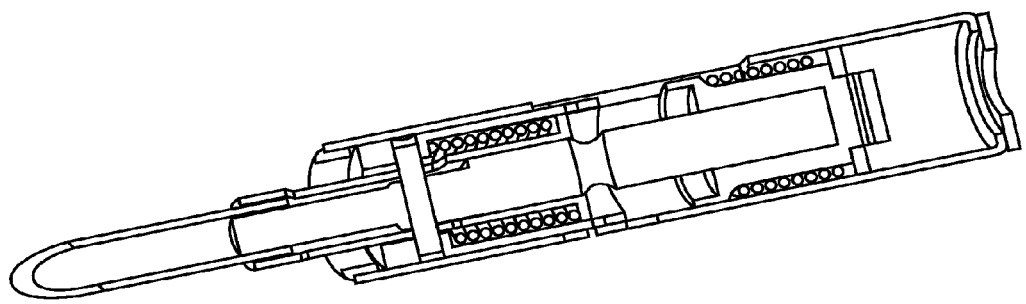
Figure 32:
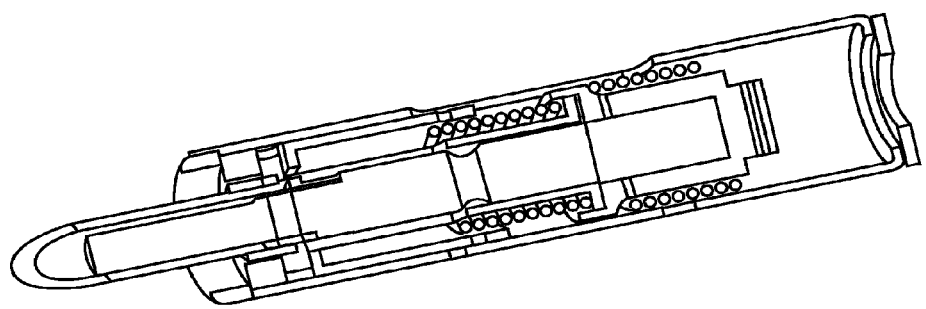

The sequence depicted in FIGS. 30-32 show three stages for the device. FIG. 30 shows the insert ready state where the device is ready for insertion of its blade. In this stage fuse wires are intact, and the actuator springs are storing mechanical energy. FIG. 31 shows the pierce state where the pierce fuse wire has vaporized, and the lancet has pierced the TM having traversed a short distance (e.g., 2 mm stroke). As shown in FIG. 21, in this stage both the pierce and the retract actuators have traveled the same short distance (e.g., 2 mm stroke) with respect to the outer shell. FIG. 32 shows the deploy and retract stage, where the retract/deploy fuse has vaporized. In this stage, the retract stage of the device moves back the short distance (e.g., 2 mm stroke) relative to the outer case and the pierce stage and the PE tube remains in the TM.

Figure 41C:
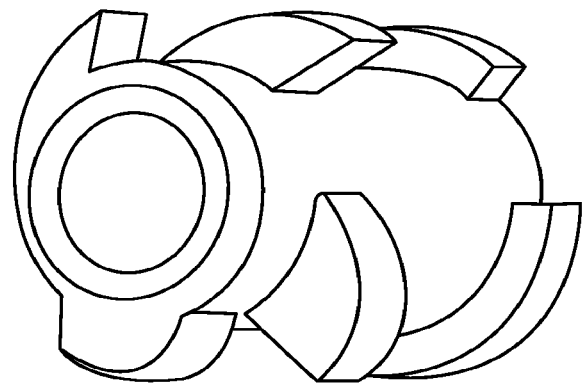
FIGS. 41A-C illustrate various PE tube shapes that include interrupted medial flanges.
Figure 41B:
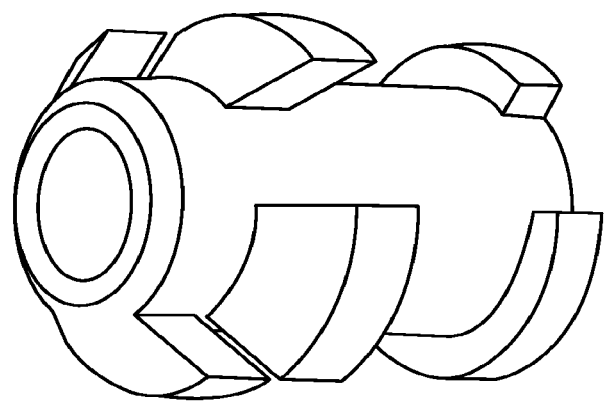
Figure 41A:
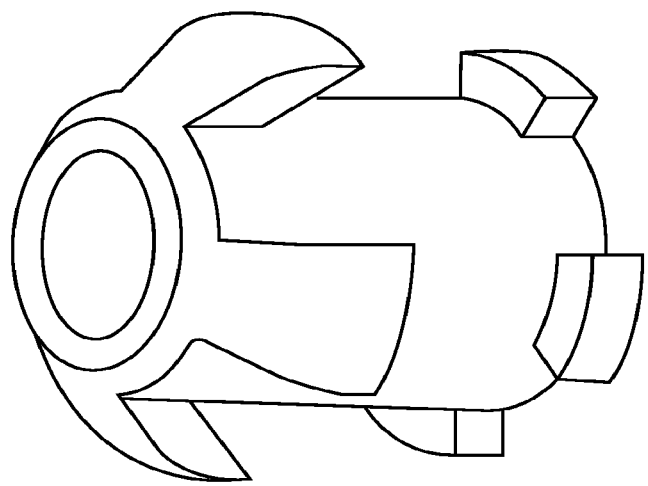

Certain aspects of the embodiments of the present invention are directed toward the unique shape of the PE tube. FIGS. 41A-C illustrate various PE tube shapes that include interrupted medial flanges that are useful in the automated insertion of the PE tubes via the PETDD.

In addition to the above two PETDD embodiments, a laser-based piercing tool can also be used to pierce the TM of the patient's ears. In addition, the PETDD may be designed such that deployment of the PE tube commences medially to the tympanic membrane and progresses to completion laterally to the membrane in such a manner that actuation of the device is accomplished from the inside out; benefits include maximizing control of PE tube deployment such that progression is in a medial-lateral direction (increasing safety) instead of lateral-medial (decreasing safety).

FIGS. 42A-B illustrate a PE tube 204A that is delivered from the inside of a cutting tool. The so-called internal PE tube is configured to be compressed for delivery inside the cutting tool; a push rod can be used to deploy the PE tube out of the cutting tool, and features of the PE tube expand to anchor it in the TM as shown in FIG. 42B. The so-called internal PE tube is advantageous because the cutting tool is configured to make a controlled incision size, and the deployment of the PE tube does not place additional stresses on the TM, since the TM is less likely to be subjected to tearing, pressure or stretching of the TM as the tube is deployed through the cutting tool. Also as shown in FIG. 43A-B, the so-called internal PE tube setup can also be used with a grommet or T-tube type PE tube designs.

FIGS. 44A-B illustrate a PE tube 204C that is delivered on the outside of a cutting tool. The so-called external PE tube can have features that help expand the incision in the TM. Such features include tapered leading edge flanges or thin or flexible internal flanges. The so-called external PE tube can be advantageous since it will enable the formation of smaller incisions. In addition, the so-called external PE tube is less dependant on the deployable features on the PE tube, as there will be no need for the internal compression of the PE tube during its storage in the PETDD device, as in the so-called internal PE tube. In addition, for the so-called external PE tube, the cutting tool can be a version of a standard myringotomy spear or blade. As shown in FIG. 44A, flanges on the push rod can prevent over insertion of the PE tube. In addition, as shown in FIG. 44C-D, flanges on the PE tube can have cut-outs to allow for the easier passage and its deflection through the TM.

Figure 37A:
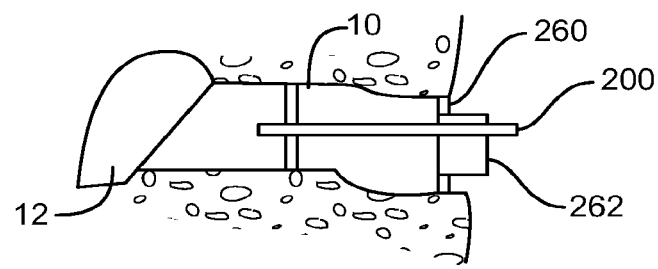
FIGS. 37A-C illustrate an embodiment of a cam/eccentric mechanism to position the PETDD in an X-Y direction.
Figure 37B:
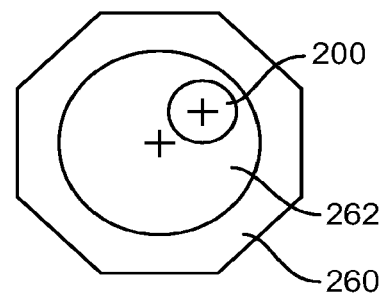
Figure 37C:
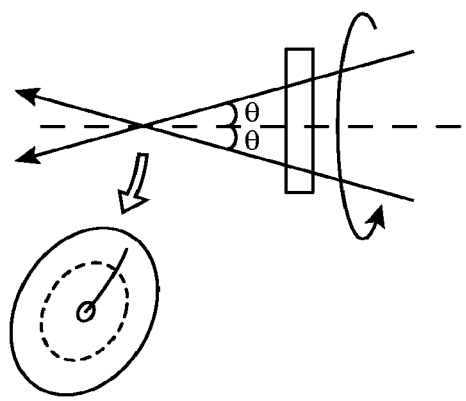

Certain aspects of the embodiments of the present invention are directed toward the use of a cam/eccentric mechanism that is used to position the PETDD in an X-Y direction. FIGS. 37A-C illustrate an embodiment of a cam/eccentric mechanism to position the PETDD in an X-Y direction. FIG. 37A shows the PETDD 200 is located within the ear canal 10, and the distal end of the PETDD is located near the TM 12. This embodiment of the PETDD includes a housing 260 that is configured to fit in the ear canal and/or portions of the guide block. The PETDD 200 is connected via a cam 262 to the housing 260. The housing 260 can be affixed to the appropriate ear structure (e.g., the external ear canal). The cam 262 is configured to rotate within the housing 260. The PETDD 200 is mounted eccentric to the cam's centerline. In operation, when the distal (i.e. medial) end of the PETDD 200 is fixed at the guide block 100, rotation of the cam 262 allows for an approximately circular sweep of the aim of the PETDD in the X-Y direction with respect to the targeting on the TM 12. As is shown in FIG. 37C, the cam-enabled embodiment of the PETDD is configured to have an aim that sweeps in a circular manner the TM 12 in a X-Y direction that is substantially parallel with the plane of the TM 12. It should be realized that the back end of cam doesn't have to be in ear canal. It can be located outside the ear. For example, when there is an "ear muff" type stabilization mechanism—the cam can be outside the ear.

The systems and devices described above can be used to practice various different procedures in addition to the ones described above. For example, the guide block system can be used to provide the ability to aspirate and suction through the working channels. In addition, a clinician may also desire to use suction to gently "pull" or steer the TM back towards the guide block and/or the PETDD which would guarantee a certain distance between the actuator and the TM to allow for a safer insertion of the PE tube.

Range Finding

Figure 33:
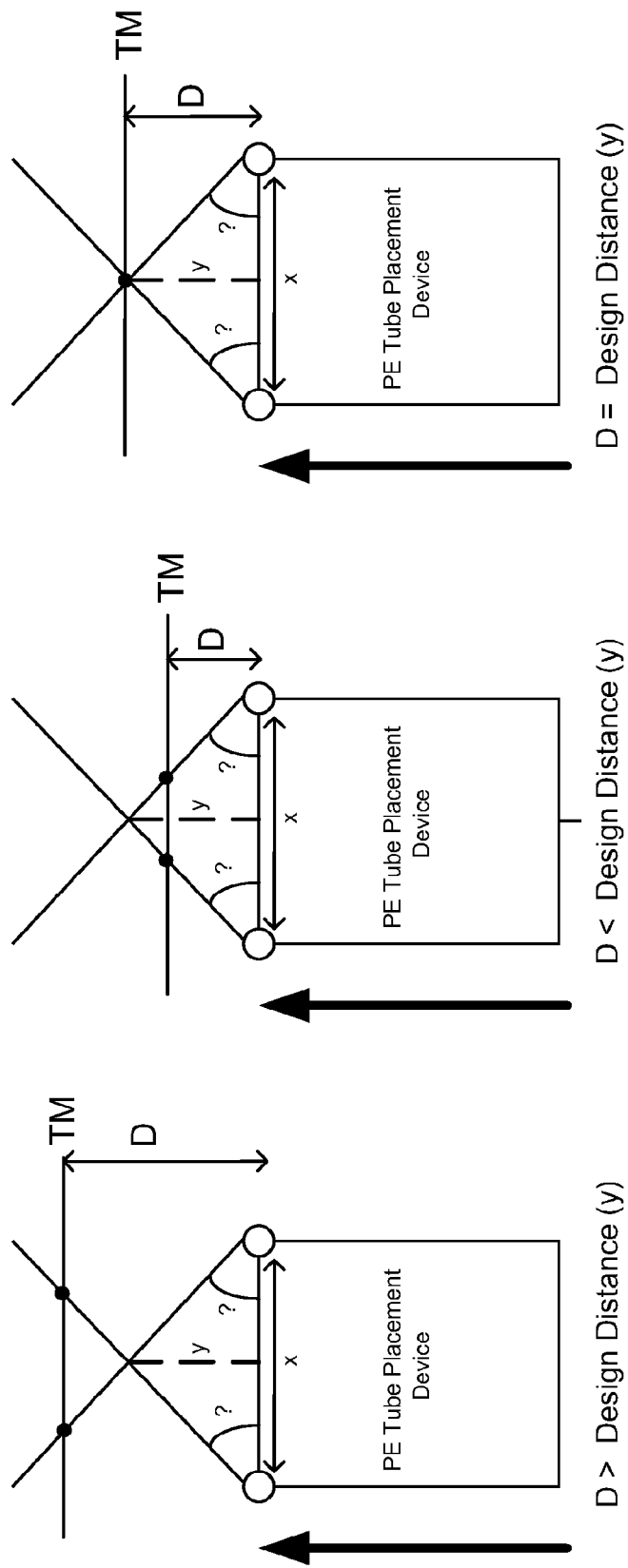
FIG. 33 illustrates one exemplary embodiment for an optical range finder for the PETDD.

In one exemplary embodiment, a light-based range finding technique can be used. The light-based system includes two light emitting elements (such as a laser) on the PE tube placement device that produce concentrated beams of light. The light emitting elements are oriented in such a way that the intersection of their produced rays is at a pre-determined distance from the PE tube placement device, as shown in FIG. 33. When the rays from the two light emitting elements are projected onto a surface, such as the TM, they produce two visible dots. As the PE tube placement device moves in a direction perpendicular to the surface of projection, the dots produced on the surface move closer together as the designed distance (y) is approached. When the designed distance is reached the two dots are coincident. Alternatively, the beams could be lines that overlap to form a cross hair at the designed distance.

Figure 34A:
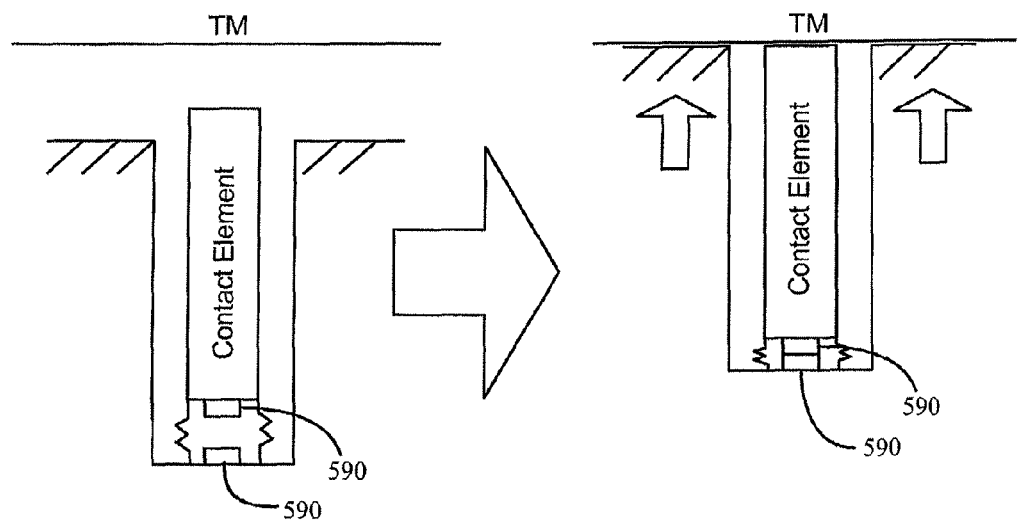
FIGS. 34A-B illustrate alternative embodiments for a range finder for the PETDD.
Figure 34B:
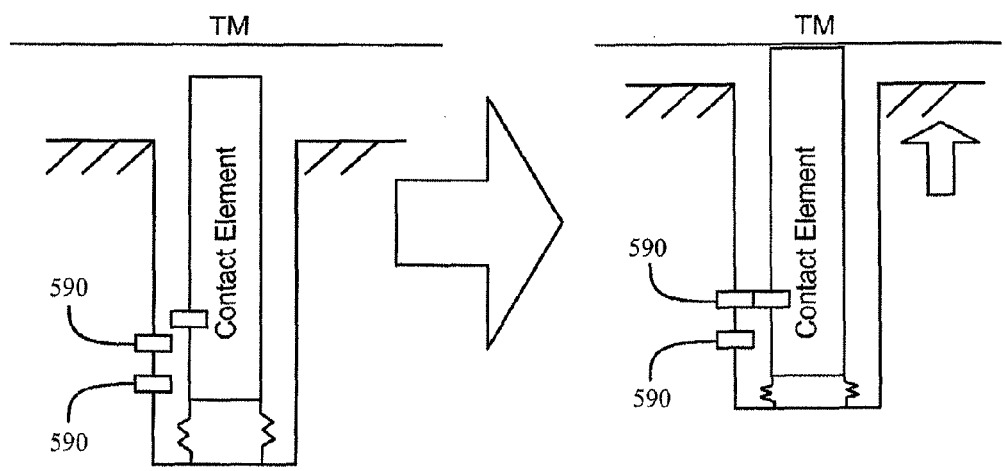

An alternative technique for range finding is shown in FIGS. 34A-B, which illustrate a contact-switch-based range finding technique. The contact switch elements 590 displace and complete a circuit—similar to a safety switch sending voltage to a terminal FIG. 34A shows the contact-switch-based range finding technique that relies on a fixed retraction distance before the circuit is closed. FIG. 34B shows the contact-switch-based range finding technique that relies on a non-fixed retraction distance before the circuit is closed. In this scheme sensors are used to determine a contact between an in-range and an out-range contact positions.

Figure 54A:
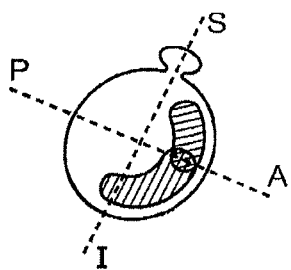
FIGS. 54A-B illustrate the X-Y targeting and the Z distance measures with respect to the ear canal.
Figure 54B:
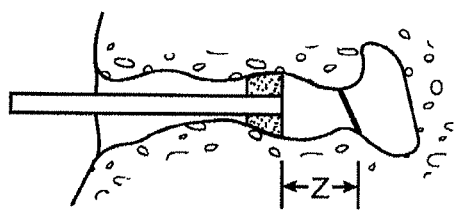

The range finding embodiments described above are used to establish an X-Y target location on the TM for PE tube placement and/or a myringotomy. The range finding embodiments are also used to establish a Z distance from the TM, within a certain range, for the safety and reliability of the PE tube delivery and/or a myringotomy. The X-Y target location and the Z distance are shown in FIGS. 54A-B. In addition to the range finding embodiments described above, the following range finding embodiments can also be used.

Figure 55A:
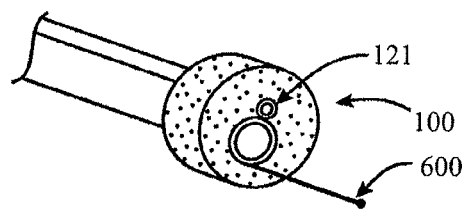
FIGS. 55A-B illustrate a range finding and targeting embodiment that includes the use of a fine hair-like element mounted on the distal end of the guide block.
Figure 55B:
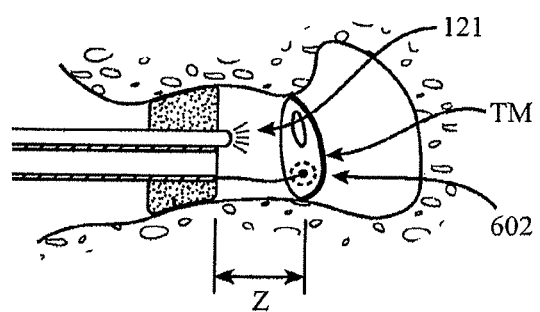

A first additional embodiment, depicted in FIGS. 55A-B, involves the use of a fine hair-like element mounted on the distal end of the guide block. When using this embodiment, the targeting and range finding can be done using an endoscope 121 by observing contact and deflection of the hair-like element 600 or whisker on the TM. In particular, targeting is achieved by observing the whisker's contact point 602 on the TM and range finding is achieved by observing the deflection of the known length of the whisker.

Figure 56A:
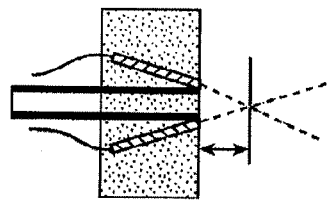
FIGS. 56A-B illustrate a range finding and targeting embodiment that involve the use of lasers.
Figure 56B:
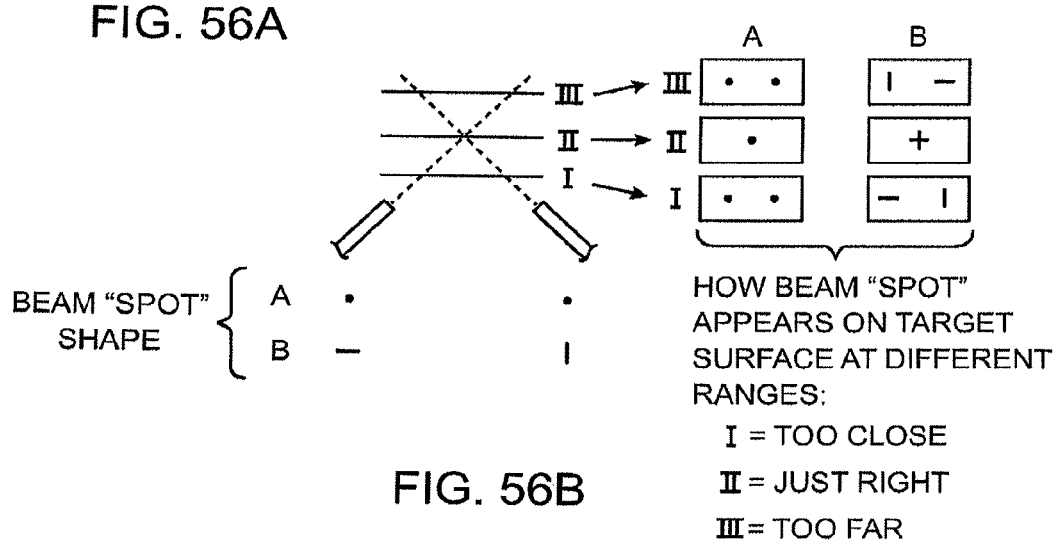

A second additional embodiment, depicted in FIGS. 56A-B, involves the use of non-contact laser targeting. As shown in FIGS. 56A-B, two laser beams are angled to coincide into a spot or crosshair when they are a certain distance from the TM. As shown in FIG. 56B, the beam can project a spot shape (A). FIG. 56B also shows how the beam spot can appear on the target surface at different ranges. When the targeting range is just right, the two beams coincide, and when the targeting distance is either too close or too far, the two beams appear as two spots. Alternatively, the beams can appear as lines that can form a cross hair. For example, when the targeting range is just right, the two beams coincide to form a cross hair, and when the targeting distance is either too close or too far, the two beams appear as two separated lines. One advantage of this laser based embodiment is that it does not contact the TM and thus can be used pre and post-anesthesia for both range finding and targeting.

Figure 57A:
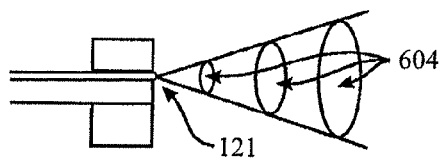
FIGS. 57A-B illustrate a range finding and targeting embodiment that involve the use of optical methods.
Figure 57B:
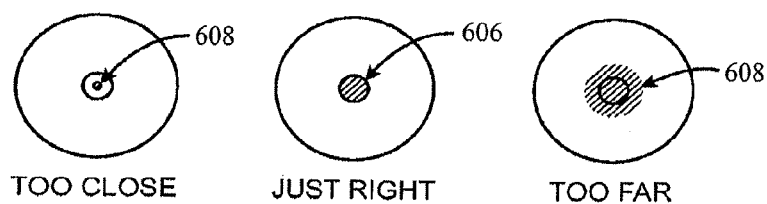

A third additional embodiment, depicted in FIGS. 57A-B, involves the use of non-contact optical targeting methods. This optical and non-contact technique can be built into the endoscope, thus eliminating the need for separate components. In one embodiment, the optical scheme can use a fixed focal length setup. In this setup, the focal length of the endoscope corresponds with the targeting range, such that when an image 604 on the endoscope screen appears focused, then targeting is within range. In another embodiment, the optical scheme can use a reticle 606 and a dot 608. In this setup, the optical beam is projected from the end of the guide block. The endoscope is configured to have a reticle 606 with a circle. When the dot or beam 608 is the same size as the circle on the reticle 606, the target is within range. When the dot or beam 608 is smaller than the circle on the reticle 606, the target is too close and when the dot or beam 608 is larger than the circle on the reticle 606, the target is too far.

In connection with the imaging configurations, a coupler can be used to attach two endoscopes to a single camera, providing imaging from two scopes simultaneously. Alternatively, a video splitter can be used to send images from two cameras to a single monitor. Since the space between the guide block and TM will be fluid filled, ultrasound can also be used for imaging. Furthermore, ultrasound can be used to drive the anesthetic across the TM and then to image the tissue region, for example while the PE tube is placed.

In addition, range finding can also be accomplished via ultrasound, radar type technology. This can be facilitated via the insertion of a medium into space to allow the ultrasoundxz/radar methods. The medium can reduce energy requirement.

Figure 35A:
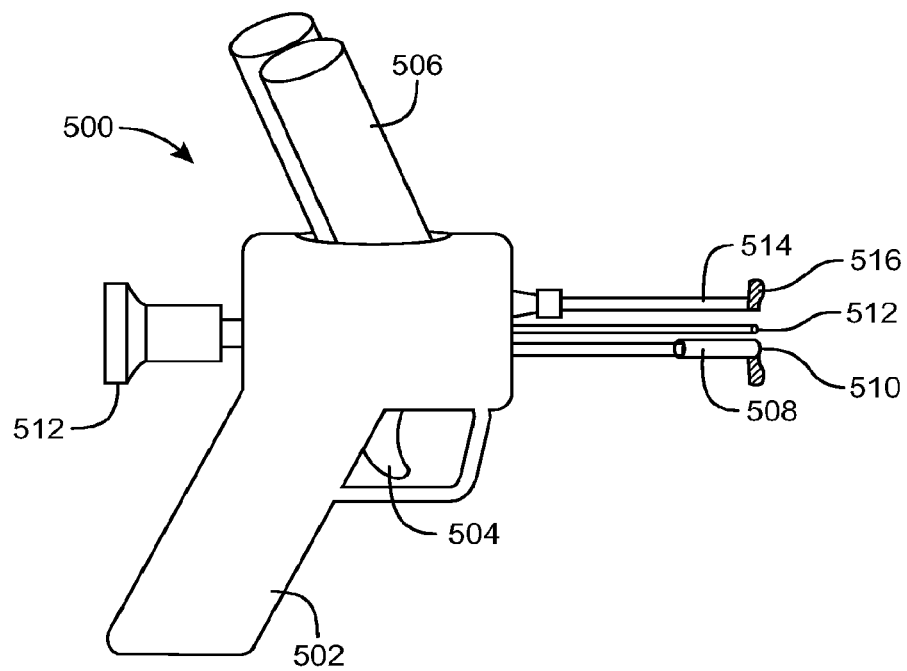
FIGS. 35A-B illustrate an embodiment of a handheld device having the combined features of an otoscope, guide tube stabilizer and range finder.
Figure 35B:
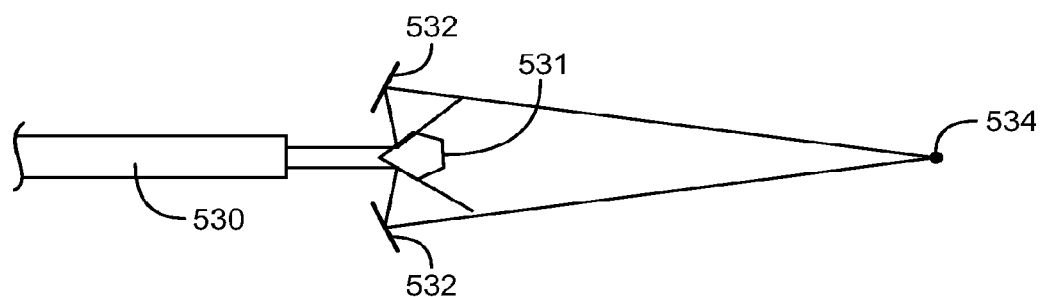

FIGS. 35A-B illustrate a handheld device 500 in accordance with one embodiment of the present invention having the combined features of an otoscope, guide tube stabilizer and range finder. As is shown in FIG. 35A, the device 500 includes a handle portion 502 that forms a part of the body of the device. The device 500 also includes a trigger 504 which can be used to actuate the otoscope, the laser range finder and/or the injection of the molding or stabilizing material. The device 500 can include a portion that is dimensioned to receive the molding material, which in one embodiment can be a two-part silicone molding material 506. The device 500 is dimensioned to hold the guide tube 508 or the one or more tubes described above. The distal end of the guide tube includes the barrier material 510. The device 500 also holds optics 512 for the direct visualization of the internal space of the ear canal. The device 500 also holds laser optics 516 that are used for range or depth finding purposes. FIG. 35B shows further details of the laser range finder 516. A laser light 530 is directed toward a splitter 531 which then directs the split laser light to mirrors 532 which then direct the laser light toward a focal point 534. With the range finder 516 distance can be set with a single laser beam through a prism 531, that splits the beam and focuses it on the focal point 534. In operation, after the device 500 has been used and removed from the ear canal, the guide tube 508 and barrier material 510 are configured to stay behind after the molding material 506 has been delivered. The device 500 can also help maintain the guide tube 508 or the one or more tubes in place in alignment prior to the injection of the molding material.

In addition to the above description, the following alternative concepts are also within the conceived embodiments of the present invention. For example, in addition to the motor and screw drive and preloaded spring embodiments described above, the drive system can be a pneumatic system, a simple solenoid-based system; or a servo solenoid-bases system. For example, the coupling between the drive system and the PETDD can be via a flexible rod or a control wire. For example, the range finder can use a capacitance contact sensor or strain contact sensor. And For example, the cutting tool can be a solid blade, a hollow lance, a screw, scissors, or a laser.

As will be understood by those skilled in the art, the present invention may be embodied in other specific forms without departing from the essential characteristics thereof. These other embodiments are intended to be included within the scope of the present invention, which is set forth in the following claim.

What is claimed is:

1. A system for treating a patient, the patient having a head with a first ear and a second ear, each ear having a tympanic membrane, the system comprising:
    (a) an input device configured to generate an electrical signal in response to entry of a command; and
    (b) a tube with a cutting edge and having a receptacle, a proximal end, a distal end, and an axis therebetween, the distal end sharpened for penetration through a tympanic membrane;
    (c) an actuation mechanism movably supporting the tube and coupled with the input device, the actuation mechanism changing from a ready state to a pierce state in response to the signal so as to cause the tube to penetrate the tympanic membrane when aligned therewith;
    (d) a tympanostomy tube supported by the actuation mechanism, wherein the tympanostomy tube is radially constrained within the receptacle of the tube, and wherein the tympanostomy tube expands radially when released;
    (e) a support system configured for maintaining alignment between the actuation mechanism and the head of the patient, wherein the input device is movably coupled to the first device so as to isolate a command movement and inhibit deviation from the alignment;
    (f) another cutting tool alignable with a tympanic membrane of the second ear;
    (g) another actuation mechanism supporting the other cutting tool, the other actuation mechanism effecting axial movement of the other cutting tool in response to the signal so as to drive the other cutting tool through the tympanic membrane of the second ear; and
    (h) circuitry coupling the input device to the actuation mechanisms such that penetration of the tympanic membranes is synchronized.

2. The system of claim 1, wherein the tympanostomy tube advances with the tube and the tube retracts back into the ear canal after releasing the tympanostomy tube.

3. The system of claim 2, wherein the signal comprises an electrical signal, the actuation mechanism comprising an electromechanical mechanism configured for effecting axial movement of the tube.

4. The system of claim 3, wherein the device comprises a first spring for urging the tube distally through the tympanic membrane and a second spring urging the tympanostomy tube free of the tube and the tube proximally, wherein the first and second springs are restrained prior to the signal and wherein the signal effects sequential release of the first spring and the second spring.

5. The system of claim 4, further comprising a damper coupled to the actuation mechanism so as to damp the axial movement of the tube.

6. The system of claim 5, wherein the first and second springs are releasably restrained by associated first and second electrically fusable members, and wherein the fusable members are coupled to the input device with a flex circuit, the flex circuit being around the axis.

7. The system of claim 3, wherein the first device comprises a shape memory alloy actuator coupled to an electrical driving circuit.

8. The system of claim 1, wherein the actuation mechanism comprises a hydraulic actuator, an electromagnetic actuator, and/or a permanent magnet actuator.

9. The system of claim 1, wherein the tube and actuation mechanism are contained within a housing having an axial length of less than 15 mm and a maximum transverse dimension of less than 5 mm.

10. A system for treating a tympanic membrane of a patient, comprising:
    (a) a tube assembly with a cutting edge configured to penetrate through a tympanic membrane and including a receptacle;
    (b) an actuation mechanism associated with the tube assembly; and
    (c) a tympanostomy tube in the receptacle, the tympanostomy tube having a first constrained configuration and a second expanded configuration and being retained in the first constrained configuration within the receptacle, wherein the tympanostomy tube is resiliently biased to assume the second expanded configuration.

11. The system of claim 10, wherein the tympanostomy tube expands radially to the second expanded configuration when released from the receptacle.

12. The system of claim 10, wherein the tympanostomy tube includes a plurality of interrupted medial flanges.

13. The system of claim 10, wherein the tympanostomy tube includes a flange with a cut-out formed therein.

14. The system of claim 10, wherein the tube assembly comprises a tube with a cutting edge, wherein the tympanostomy tube is configured about the tube with the cutting edge.

15. The system of claim 10, wherein the tympanostomy tube includes a distal end with a radially extending flange.

16. The system of claim 15, wherein the tympanostomy tube includes a proximal end with a radially extending flange.

17. The system of claim 10, wherein the tympanostomy tube has a distal end including a tapered structure.

18. The system of claim 10, wherein the tympanostomy tube has a distal end including flexible flanges.

19. A system for treating a tympanic membrane of a patient, comprising:
    (a) a tube deployment assembly, wherein the tube deployment assembly includes a piercing element configured to penetrate through a tympanic membrane, wherein the tube deployment assembly further defines a receptacle;
    (b) an actuation mechanism associated with the piercing element, wherein the actuation mechanism is operable to drive the piercing element distally; and
    (c) a tympanostomy tube positioned in the receptacle, wherein the tympanostomy tube is resiliently biased to assume an expanded configuration, wherein the receptacle is configured to hold the tympanostomy tube in a non-expanded configuration.

* * * * *